US011564580B2

(12) United States Patent
Fransen et al.

(10) Patent No.: US 11,564,580 B2
(45) Date of Patent: Jan. 31, 2023

(54) HOUSING COMPRISING A SENSOR

(71) Applicant: Sonion Nederland B.V., Hoofddorp (NL)

(72) Inventors: Alwin Fransen, Hoofddorp (NL); Nicolaas Maria Jozef Stoffels, Hoofddorp (NL); Paul Christiaan van Hal, Hoofddorp (NL); Sietse Jacob van Reeuwijk, Hoofddorp (NL); Raymond Mögelin, Hoofddorp (NL)

(73) Assignee: Sonion Nederland B.V., Hoofddorp (NL)

( * ) Notice: Subject to any disclaimer, the term of this patent is extended or adjusted under 35 U.S.C. 154(b) by 644 days.

(21) Appl. No.: 16/549,733

(22) Filed: Aug. 23, 2019

(65) Prior Publication Data

US 2020/0085326 A1  Mar. 19, 2020

(30) Foreign Application Priority Data

Sep. 19, 2018 (EP) ..................................... 18195529

(51) Int. Cl.
*A61B 5/022* (2006.01)
*A61B 5/024* (2006.01)
*H04R 1/28* (2006.01)
*H04R 1/10* (2006.01)
*A61B 5/00* (2006.01)
*H04R 25/00* (2006.01)

(52) U.S. Cl.
CPC ........ *A61B 5/02416* (2013.01); *A61B 5/6817* (2013.01); *H04R 1/1016* (2013.01); *H04R 1/1091* (2013.01); *H04R 1/2838* (2013.01); *H04R 25/60* (2013.01); *H04R 1/1083* (2013.01); *H04R 2460/01* (2013.01)

(58) Field of Classification Search
CPC ..... A61B 1/227; A61B 5/022; A61B 5/02416; A61B 5/14532; A61B 5/6817; A61B 5/6898; A61B 5/7207; A61B 5/721; H04R 1/105; H04R 1/1016; H04R 1/1083; H04R 1/1091; H04R 1/2838; H04R 5/04; H04R 25/60; H04R 25/603; H04R 2460/01; H04R 2225/023; H04R 2225/025
USPC ................ 600/323, 473, 476, 479, 500, 559
See application file for complete search history.

(56) References Cited

U.S. PATENT DOCUMENTS

| 5,823,966 A | * | 10/1998 | Buchert | ............. A61B 5/14532 374/E13.003 |
| 6,647,284 B1 | * | 11/2003 | Lee | ........................... G01J 5/02 374/E1.013 |
| 6,788,796 B1 | | 9/2004 | Miles | |

(Continued)

FOREIGN PATENT DOCUMENTS

| EP | 3073765 A1 | 9/2016 |
| WO | WO 2017/027551 A1 | 2/2017 |

*Primary Examiner* — Gerald Gauthier
(74) *Attorney, Agent, or Firm* — Nixon Peabody LLP

(57) ABSTRACT

An assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing. No overlap may be provided between the field of view of the radiation detector(s) and the emitter(s), such as by providing a blocking element.

13 Claims, 4 Drawing Sheets

(56) References Cited

U.S. PATENT DOCUMENTS

| | | |
|---|---|---|
| 6,831,577 B1 | 12/2004 | Furst |
| 6,853,290 B2 | 2/2005 | Jorgensen |
| 6,859,542 B2 | 2/2005 | Johannsen |
| 6,888,408 B2 | 5/2005 | Furst |
| 6,914,992 B1 | 7/2005 | van Halteren |
| 6,919,519 B2 | 7/2005 | Ravnkilde |
| 6,930,259 B1 | 8/2005 | Jorgensen |
| 6,943,308 B2 | 9/2005 | Ravnkilde |
| 6,974,921 B2 | 12/2005 | Jorgensen |
| 7,008,271 B2 | 3/2006 | Jorgensen |
| 7,012,200 B2 | 3/2006 | Moller |
| 7,062,058 B2 | 6/2006 | Steeman |
| 7,062,063 B2 | 6/2006 | Hansen |
| 7,072,482 B2 | 7/2006 | Van Doorn |
| 7,088,839 B2 | 8/2006 | Geschiere |
| 7,110,560 B2 | 9/2006 | Stenberg |
| 7,136,496 B2 | 11/2006 | van Halteren |
| 7,142,682 B2 | 11/2006 | Mollenborn et al. |
| 7,181,035 B2 | 2/2007 | van Halteren |
| 7,190,803 B2 | 3/2007 | van Halteren |
| 7,206,428 B2 | 4/2007 | Geschiere |
| 7,221,767 B2 | 5/2007 | Mullenborn |
| 7,221,769 B1 | 5/2007 | Jorgensen |
| 7,227,968 B2 | 6/2007 | van Halteren |
| 7,239,714 B2 | 7/2007 | de Blok |
| 7,245,734 B2 | 7/2007 | Niederdraenk |
| 7,254,248 B2 | 8/2007 | Johannsen |
| 7,286,680 B2 | 10/2007 | Steeman |
| 7,292,700 B1 | 11/2007 | Engbert |
| 7,292,876 B2 | 11/2007 | Bosh |
| 7,336,794 B2 | 2/2008 | Furst |
| 7,376,240 B2 | 5/2008 | Hansen |
| 7,403,630 B2 | 7/2008 | Jorgensen |
| 7,415,121 B2 | 8/2008 | Mögelin |
| 7,425,196 B2 | 9/2008 | Jorgensen |
| 7,460,681 B2 | 12/2008 | Geschiere |
| 7,466,835 B2 | 12/2008 | Stenberg |
| 7,492,919 B2 | 2/2009 | Engbert |
| 7,548,626 B2 | 6/2009 | Stenberg |
| 7,657,048 B2 | 2/2010 | van Halteren |
| 7,684,575 B2 | 3/2010 | van Halteren |
| 7,706,561 B2 | 4/2010 | Wilmink |
| 7,715,583 B2 | 5/2010 | Van Halteren |
| 7,728,237 B2 | 6/2010 | Pedersen |
| 7,747,032 B2 | 6/2010 | Zei |
| 7,809,151 B2 | 10/2010 | Van Halteren |
| 7,822,218 B2 | 10/2010 | Van Halteren |
| 7,899,203 B2 | 3/2011 | Van Halteren |
| 7,912,240 B2 | 3/2011 | Madaffari |
| 7,946,890 B1 | 5/2011 | Bondo |
| 7,953,241 B2 | 5/2011 | Jorgensen |
| 7,961,899 B2 | 6/2011 | Van Halteren |
| 7,970,161 B2 | 6/2011 | van Halteren |
| 7,995,782 B2 | 8/2011 | Saltykov |
| 8,098,854 B2 | 1/2012 | van Halteren |
| 8,101,876 B2 | 1/2012 | Andreasen |
| 8,103,039 B2 | 1/2012 | van Halteren |
| 8,160,290 B2 | 4/2012 | Jorgensen |
| 8,170,249 B2 | 5/2012 | Halteren |
| 8,189,804 B2 | 5/2012 | Hruza |
| 8,189,820 B2 | 5/2012 | Wang |
| 8,223,996 B2 | 7/2012 | Beekman |
| 8,233,652 B2 | 7/2012 | Jorgensen |
| 8,259,963 B2 | 9/2012 | Stenberg |
| 8,259,976 B2 | 9/2012 | van Halteren |
| 8,259,977 B2 | 9/2012 | Jorgensen |
| 8,280,082 B2 | 10/2012 | van Halteren |
| 8,284,966 B2 | 10/2012 | Wilk |
| 8,313,336 B2 | 11/2012 | Bondo |
| 8,315,422 B2 | 11/2012 | van Halteren |
| 8,331,595 B2 | 12/2012 | van Halteren |
| 8,369,552 B2 | 2/2013 | Engbert |
| 8,379,899 B2 | 2/2013 | van Halteren |
| 8,509,468 B2 | 8/2013 | van Halteren |
| 8,526,651 B2 | 9/2013 | Lafort |
| 8,526,652 B2 | 9/2013 | Ambrose |
| 8,700,111 B2 | 4/2014 | LeBoeuf |
| 9,106,999 B2 | 8/2015 | Darlington |
| 9,654,854 B2 | 5/2017 | Darlington |
| 9,794,653 B2 | 10/2017 | Aumer |
| 10,003,882 B2 | 6/2018 | Urup |
| 10,219,069 B2 | 2/2019 | Urup |
| 11,375,326 B2 * | 6/2022 | Blumer ............... H04R 1/1016 |
| 2010/0191144 A1 * | 7/2010 | Zoth ................... A61B 1/227 |
| | | 600/559 |
| 2011/0069852 A1 * | 3/2011 | Arndt ................... H04R 25/48 |
| | | 381/328 |
| 2011/0182453 A1 | 7/2011 | van Hal |
| 2011/0189880 A1 | 8/2011 | Bondo |
| 2011/0299708 A1 | 12/2011 | Bondo |
| 2011/0299712 A1 | 12/2011 | Bondo |
| 2011/0311069 A1 | 12/2011 | Ambrose |
| 2012/0014548 A1 | 1/2012 | van Halteren |
| 2012/0027245 A1 | 2/2012 | van Halteren |
| 2012/0140966 A1 | 6/2012 | Mocking |
| 2012/0155683 A1 | 6/2012 | van Halteren |
| 2012/0155694 A1 | 6/2012 | Reeuwijk |
| 2012/0255805 A1 | 10/2012 | van Halteren |
| 2013/0028451 A1 | 1/2013 | de Roo |
| 2013/0131519 A1 * | 5/2013 | Le ..................... A61B 5/0013 |
| | | 600/476 |
| 2013/0136284 A1 | 5/2013 | van Hal |
| 2013/0142370 A1 | 6/2013 | Engbert |
| 2013/0163799 A1 | 6/2013 | Van Halteren |
| 2013/0195295 A1 | 8/2013 | van Halteren |
| 2015/0237429 A1 | 8/2015 | Ryan |
| 2015/0257662 A1 * | 9/2015 | Lee ..................... A61B 5/7207 |
| | | 600/323 |
| 2016/0198964 A1 * | 7/2016 | Lee ..................... A61B 5/6898 |
| | | 600/479 |
| 2017/0014056 A1 * | 1/2017 | Newberry ............ A61B 5/0022 |
| 2017/0078785 A1 * | 3/2017 | Qian ................... H04R 1/406 |
| 2018/0042554 A1 | 2/2018 | Wagner |
| 2019/0029593 A1 * | 1/2019 | Orron ................. H04R 1/105 |
| 2020/0085326 A1 * | 3/2020 | Fransen ............... H04R 25/60 |

\* cited by examiner

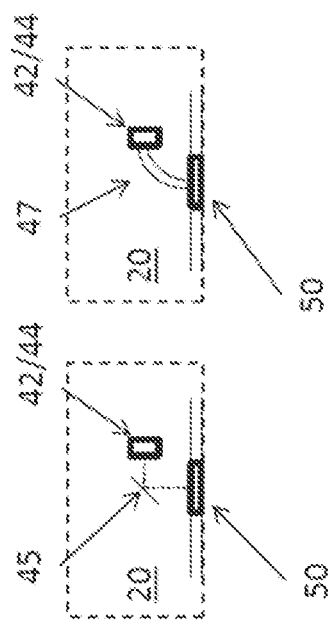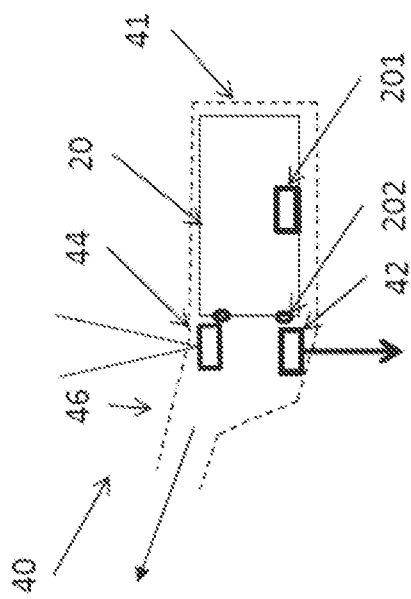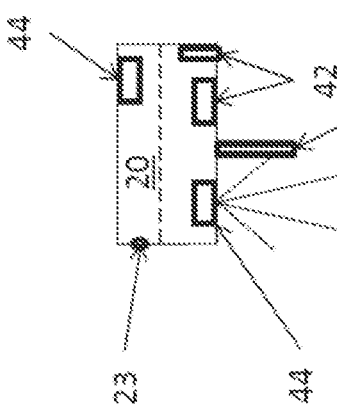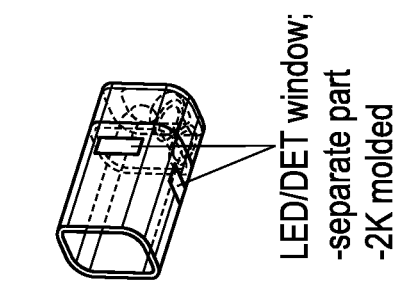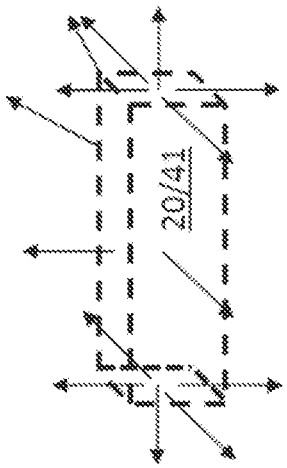

HOUSING COMPRISING A SENSOR

The present invention relates to a housing comprising a sensor comprising one or more radiation emitters and one or more detectors. The housing may be configured to be positioned in an ear canal of a person where the sensor may be a so-called PPG sensor.

Technology of this type may be seen in U.S. Pat. No. 8,700,111, US2018/0042554, U.S. Pat. No. 9,794,653, U.S. Ser. No. 10/219,069, U.S. Ser. No. 10/003,882, U.S. Pat. No. 7,747,032, US2015237429, U.S. Pat. No. 7,995,782, EP3073765, U.S. Pat. Nos. 9,106,999 and 9,654,854.

In a first aspect, the invention relates to an assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing.

Preferably, the detector(s) and emitter(s) form a sensor system.

In this context, an assembly of a sensor and a housing may, in addition to the sensor and housing, comprise also other elements such as receiver(s), amplifier(s), processor(s), battery, optical components, electrical connections (e.g. (flex)pcb), other transducers (actuators, sensors) or the like. The sensor and housing may be attached to each other or not. In one situation, the sensor is provided inside the housing.

Also, the present assembly is especially suited for positioning in the ear canal of a person where sensors may be used for a number of purposes. One purpose is to determine the pulse or other physiological signs of a person like blood pressure, heart rate variability or respiration rate, such as using the so-called PPG (photoplethysmography) which relates to absorption, reflection and/or scattering of radiation in the tissue, including blood vessels. On the basis of the radiation received, the pulse or other physiological parameters of the person may be determined, as the absorption, reflection and/or scattering in the tissue will vary with the perfusion of the tissue and expansion/contraction of the blood vessels. Thus, the variation of received radiation will correspond to the physiological parameters of the person like pulse frequency, blood pressure etc.

As the absorption, reflection and/or scattering of radiation in the tissue also depends on other tissue parameters than perfusion, PPG can also be used to determine other biological parameters like changes in oxygenation of the blood.

The emitter(s) is/are configured or positioned to emit radiation away from the housing. Clearly, an emitter may emit radiation within a fan or cone (of any cross sectional shape) or another light distribution pattern, where some of the radiation may be emitted toward or along the housing but where at least some of the radiation is emitted in a direction away from the housing. An emission cone may be defined by directions from the emitter toward the surroundings where a particular output intensity or intensity portion, such as half the maximum intensity output in a direction from the emitter, is seen. In one situation, the emission cone may be defined as the FWHM (full width half maximum; see below) of the emitter, i.e. the cone inside of which the intensity per area is higher than half the maximum intensity per area. In that situation, the cone is defined where half the maximum intensity is output per area. Clearly, the cone may be defined by any percentage of the maximum intensity output per area.

The detector(s) is/are also configured to or positioned to receive radiation directed toward the housing. The detector(s) may have a field of view which may also be defined as a cone or other shape, where the field of view can be defined as the set of angles (or the 3D shape) inside which the detection efficiency is higher than half the maximum detection efficiency of the detector. Also in this situation may the field of view be defined by any percentage of the maximum sensitivity.

The housing is configured to be positioned inside an ear canal of a person. In this situation, the housing preferably has a volume not exceeding 1000 $mm^3$, such as not exceeding 500 or even 250 $mm^3$. The housing may be oblong and have a longitudinal axis. The length along the longitudinal axis may be 15 mm or less, such as 11 mm or less. In a plane perpendicular to the longitudinal axis, the housing may have an area not exceeding 64 $mm^2$, such as not exceeding 30 $mm^2$ and/or have a longest dimension not exceeding 15 mm, such as not exceeding 12 mm, 9 mm or 7 mm.

As mentioned, the sensor may now be an optical sensor which may be used for e.g. determining a pulse or other physiological signs of a person using the so-called PPG technique. This sensor has at least a radiation emitter and a radiation detector. Clearly, the radiation may be selected according to a desired measurement or detection. The PPG technique relates to absorption, scattering and/or reflection of the tissue as, in case of the detection of e.g. blood pressure or heartrate), a function of the perfusion of the tissue caused by the action of the heart. Other parameters may be determined from radiation absorption or the like. Thus, the wavelength of the radiation may be selected for the particular purpose.

Then, the radiation emitter of course will also be selected depending on the purpose. Radiation emitters may emit a broad spectrum of radiation, a more narrow spectrum, or only one or two wavelengths as desired. LEDs, laser diodes and the like may be used. Of course, optical fibres, filters, gratings, mirrors, lenses, windows and the like may be provided for guiding and adapting the radiation, such as if the output characteristics, such as the output cone size/angle of the actual radiation emitter is not as desired.

Optical filters can be used to minimize detection of unwanted signals, like the radiation from external light sources (e.g. sunlight).

The detector also will be selected based on the purpose and the radiation wavelength. Also, some detector types are faster reacting than others and some types are able to detect lower intensities than others. Again, lenses and the like may be used for adapting the field of view, if desired, or for collecting radiation and guiding it to the detector.

In one embodiment, the method comprises connecting the emitter(s) and detector(s) to the housing. In this manner, handling of the assembly is easier, and relative positioning and directing of the detectors and emitters—and the housing, is made easy.

Often, a receiver is present in the assembly housing. The receiver is a sound generator so that the housing forms a hearing device or part of a hearing device. In one embodiment, the assembly forms an RIC (Receiver In Canal), mounted in the ear canal by means of e.g. a dome or (custom) mould for generating sound to the inner ear. Other embodiments might be the ITE (In The Ear) hearing instrument or earbud. This RIC, ITE, earbud or alike may then have the additional function provided by the sensor.

In one embodiment, one or more of the detector(s) and/or one or more of the emitter(s) is/are configured to be directed at least substantially in a vertical direction, such as when positioned in an ear canal of a person in an upright position looking and straight ahead or when the person is in any other position.

Clearly, all aspects, embodiments and situations of the invention may be combined in any manner. Any number of aspects/embodiments/situations may be combined.

In this connection, the vertical direction may be within 45 degrees of vertical, such as within 30, 25, 20, 15, 10 or 5 degrees from vertical (such as a vector or direction of gravity).

Preferably, the direction is downwardly directed.

It may be preferred that the housing engages the ear canal at this (vertical) position so that there is no distance and/or a reduced loss of radiation between the emitter/detector and the ear canal tissue.

Often, a person's ear canal is more or less oval in cross section where the longest axis or dimension is upwardly/downwardly directed. Naturally, the shape need not be completely oval, but may be easily fitted to an oval shape. Then, this one or more detector(s) and/or emitter(s) may be directed along the major axis of this ovality or a longest cross sectional dimension of the ear canal cross section.

In one embodiment, the method comprises the step of positioning the assembly in the ear canal of a person so that one or more of the detector(s) and/or one or more of the emitter(s) is/are directed at least substantially in a vertical direction.

As mentioned, this direction may be a downward direction and/or along a largest dimension of an oval cross section of the ear canal.

For some types of sensing, such as when based on absorption, it is desired to have an overlap in the field(s) of view of the detector(s) and the emission cone(s) of the emitter(s). For other types of sensing this is not that important, such as when the determination is based on reflection/scattering where radiation may be scattered from an emission cone to a field of view.

In some types of sensing, it is desired that if the fields of view of the detector(s) and the cone(s) of the emitter(s) overlap, this overlap is positioned farther away from the detector/emitter than a predetermined distance. This may be the situation in PPG measurements as it is desired that the radiation detected has traveled a minimum distance in the tissue before detection. This may be achieved by either positioning the emitter/detector far from each other and/or by directing them in different directions, for example.

In one embodiment:
one of the radiation detectors is positioned in or at the housing and has a field of view defining a view axis,
one of the radiation emitters is positioned in or at the housing and has an emission cone defining an emission axis.

Naturally, a field of view and/or emission cone may be defined by the emitter/detector itself and/or optics or other elements positioned in the path of the radiation. A lens will often change the path of the radiation and thus the field of view or the cone.

It may be desired to provide the detector(s) and/or emitter(s) in or at the housing wall in order to allow transport of the radiation to/from the surroundings of the housing. Alternatively or additionally, one or more windows transparent to the radiation may be provided in the housing to allow radiation from the emitter to exit the assembly housing and/or radiation from outside of the assembly housing to reach the detector.

Naturally, the detector will define an angle or field of view within which it is able to successfully receive or detect radiation. This angle will have a central view axis which usually is a symmetry axis of the detector. Naturally, a mirror, lens or the like may be provided in front of the detector so that the axis is instead defined by this mirror/lens. The light-guiding to change angle at which light exits/enters the RIC may be seen in U.S. provisional application No. 62/733,327.

The same is the case for the emitter which will emit the radiation within a cone, typically, which again will have a central emission axis again typically being a symmetry axis of the emitter, for example perpendicularly to an emitting surface of the emitter. Also here, a lens or the like may be provided in front of the emitter so that the output cone is defined by this lens instead.

In one situation, there is no overlap between the field of view and the emission cone. In this situation, the radiation needs to be scattered or reflected at least once (if it is not absorbed and other radiation, such as radiation emitted by the tissue is detected).

Naturally, the emitter(s) and detector(s) need not be provided at/in the same side of the housing or on different sides thereof. Due to radiation being reflected/scattered, the radiation may still travel from the emitter to the detector even when it has to travel around the housing or around a corner thereof.

In one situation, no overlap exists between the field of view and the emission cone within a distance of 0 or 1 mm from the housing, such as within a distance of 2, 3, 4, 5 or 6 mm from the housing. In this manner, it may be imposed on the radiation that it needs to travel a minimum distance within the tissue.

A distance between an emitter or detector and a surface of a tissue of ear canal may vary between 0 mm (e.g. in case of a custom mold type of hearing device, e.g. ITE, a RIC with a custom dome, or e.g. in case at some portions of ear canal a RIC touches the surface of ear canal), or up to 6-15 mm depending on a size of a person's ear canal.

In one situation, the housing comprises at least a first and a second non-overlapping surface parts directed in different directions, where:
the view axis of one of the detector(s) extends at an angle, such as an angle in the interval of 30-160 degrees, such as within the interval of 45-135 degrees, such as around 90 degrees, to the first surface part and
the emission axis of one of the emitter(s) extends at an angle, such as an angle in the interval of 30-160 degrees, such as within the interval of 30-160 degrees, such as within the interval of 45-135, such as around 90 degrees to the second surface part.

The two surface parts may have general directions (such as a normal vector to the surface part) with an angle between them, such as an angle in the interval of 30-160 degrees, such as within the interval of 45-135 degrees, such as around 90 degrees.

In this situation, positioning the emitter at or in one wall, such as when emitting radiation along a central axis perpendicular to that wall, positioning the receiver on or at an adjacent wall with a central axis perpendicular to that wall, the axes of the receiver and emitter will be perpendicular to each other.

In one situation, a minimum distance of 2 mm, such as 3 mm, such as 4 mm, such as 5 mm, such as at least 6 mm exists between an emitter and a detector. This distance usually is along the outer surface of the housing and from a centre of the detector to a centre of the emitter. The distance may be along a straight wall portion or along a bent outer surface, such as over an edge or corner. The distance may be the shortest distance between the emitter and the detector.

In another embodiment, a detector and an emitter are provided in or at the same side surface, where an angle of no less than 5 degrees, such as at least 10 degrees exists between the view angle and emission angle. Preferably, the view angle and emission angle point away from each other. In this situation, there may or may not be an overlap between the field of view and the cone, depending on the width of the field of view and cone around the respective axis.

In situations where e.g. a minimum distance between emitter and detector is not possible or realistic due to the housing or surface being very small, this relative angling may ensure that the overlap is not present or is present only sufficiently far from the housing.

In one embodiment, the housing has 6 surface portions, pairwise at least substantially parallel, where each pair of surface portions are at least substantially perpendicular to the other pairs of surface portions, the first surface portion being one of the 6 surface portions.

The housing may have rounded corners and edges. Detector(s) and/or emitters may also be provided on or at edges or corners.

In one embodiment, the second surface portion extends between at least two of the 6 surface portions and has a non-zero angle to each of the at least two of the 6 surface portions.

In one embodiment of the method:
one of the radiation detectors detects radiation within a field of view defining a view axis,
one of the radiation emitters emits radiation within an emission cone defining an emission axis.

Then, there may be no overlap between the field of view and the emission cone.

Alternatively, no overlap may exist between the field of view and the emission cone within a distance of 1 mm from the housing.

The housing may comprise at least a first and a second non-overlapping surface parts directed in different directions, where:
the view axis of one of the detector(s) extends at an angle, such as an angle in the interval of 30-160 degrees, such as within the interval of 45-135 degrees, such as around 90 degrees, to the first surface part and
the emission axis of one of the emitter(s) extends at an angle, such as an angle in the interval of 30-160 degrees, such as within the interval of 30-160 degrees, such as within the interval of 45-135, such as around 90 degrees to the second surface part.

One aspect of the invention relates to an assembly of a receiver, a radiation emitter, a radiation detector and an assembly housing, wherein:
the receiver has a receiver housing and is positioned inside the assembly housing,
the radiation detector is positioned in the assembly housing and has a reception direction or view axis along a first direction,
the radiation emitter is positioned in the assembly housing and has an emission direction or axis along a second direction, an angle existing between the first and second directions,
one or more windows transparent to the radiation are provided in the assembly housing for allowing radiation from the emitter to exit the assembly housing and radiation from outside of the assembly housing to reach the detector.

Then, the assembly housing may be arranged to have the radiation emitter or radiation detector positioned in ear canal to allow radiation to exit towards or enter from the direction towards the bottom of the ear canal.

In one situation:
one of the radiation detectors is positioned in the housing and has a field of view, and
one of the radiation emitters is positioned in the housing and has an emission cone,
where a (minimum) distance of at least 1 mm, such as at least 2 mm, such as at least 3 mm, such as at least 4 mm, such as at least 5 mm, such as at least 6 mm, such as at least 7 mm, such as at least 8 mm exists between the field of view and the cone, within a distance of at least 1 mm, such as at least 2 mm, such as at least 3 mm from the housing.

This may be in order to have the received intensity sufficiently low to not overpower the detector or in order to have a sufficient overlap or travelling distance in the tissue to arrive at a sufficient interaction with the tissue to be able to discern the parameter sought for. This may be achieved by positioning the detector and emitter so that there is no or minimal overlap in their field of view and the cone within a certain distance from the emitter/detector. This may be achieved by providing a distance between the emitter and detector or by angling these away from each other.

Requiring a minimum distance will ensure that a desired minimum proportion of the radiation interacts with the tissue until reaching the detector. Also, radiation reaching the detector after having traveled a too small distance in the tissue, might contain too little useful signal such that the signal level (radiation modulation by biological parameters like perfusion) is too low compared to the (inherent) system noise, yielding a too low signal-noise ratio (SNR).

In one situation, the housing is configured to engage an ear canal at a position comprised within the field of view or the cone. In this situation, a good interface may be obtained for guiding the radiation into the tissue. Also, when the tissue engages the housing at this position, a good control is obtained of how far the radiation travels through the tissue.

In one situation, the field of view and/or cone is defined by a window and/or a lens at the outer surface of the housing. In that situation, even a displacement between the emitter/detector and the housing may be handled by the action of the window/lens.

In one embodiment of the method:
one of the radiation detectors receives radiation within a field of view,
one of the radiation emitters emits radiation within an emission cone,
where a (minimum) distance of at least 1 mm, such as at least 2 mm, such as at least 3 mm, such as at least 4 mm, such as at least 5 mm, such as at least 6 mm, such as at least 7 mm, such as at least 8 mm exists between the field of view and the cone, within a distance of at least 1 mm, such as at least 2 mm, such as at least 3 mm from the housing.

Then, the housing may engage an ear canal at a position comprised within the field of view or the cone.

Also, the field of view and/or cone may be defined by a window and/or a lens at the outer surface of the housing.

In one embodiment, the assembly further comprises a receiver having a receiver housing, wherein at least one of the one or more detectors and one or more emitters is attached to the receiver housing.

A receiver is a sound generator and may be based on any desired technology, such as moving magnet, moving coil, balanced armature, electret technology, MEMS technology, piezo technology or the like. The receiver is preferably configured to receive a signal, such as an electrical signal, and output sound or vibration with corresponding frequency contents, at least within a desired frequency interval.

Preferably, the receiver is a miniature receiver, such as a sound generator with a largest dimension of no more than 10 mm, such as no more than 8 mm, such as no more than 6 mm or no more than 5 mm. In one situation, the sound generator housing may have a volume of no more than 100 mm$^3$, such as no more than 70 mm$^3$, such as no more than 50 mm$^3$, such as no more than 30 mm$^3$. Miniature sound generators may be used in hearing aids, hearables or personal hearing devices, such as ear phones or the like.

The receiver often has a diaphragm defining, with an inner surface of the receiver housing, the first chamber in the receiver housing. Often, another chamber is defined at least partly by the other side of the diaphragm and the inner surface of the housing. The sound output often extends from inside of the receiver housing and to the outside thereof, such as from the first and/or other chamber, so that sound generated by the diaphragm may escape the receiver housing via the sound output.

The sound output is provided in a housing wall part of the receiver housing, typically a flat or plane wall part of the receiver housing.

Usually, a diaphragm is flat or plane or at least extends in a plane, which is defined as the first plane. The diaphragm may be curved or have indentations or ridges, so that the first plane may be a symmetry plane, a lower plane, an upper plane, a plane in which the diaphragm is supported, such as at its edges, or the like.

In one embodiment, the assembly comprises also additional parts, such as a spout, a dome, a sound channel or the like, where the assembly according to the first aspect is attached to the sound channel, dome, spout or the receiver housing, an where one of the emitter and detector is provided in/at the outer housing and/or receiver housing as described in relation to the first aspect and where the second of the emitter and detector is attached to another portion of the outer assembly, such as the outer device housing, dome, sound channel, spout or the like.

Domes may be used for keeping the housing in the desired position. Single domes, double domes, custom domes, custom moulds may be provided. An alternative it the so-called sportslock.

In one situation, the assembly further comprises a first window or lens in the receiver housing and a second window or lens in either the housing or an element, such as a dome or spout, attached to the housing, wherein an emitter is positioned so as to emit radiation toward one of the first and second window/lens and a detector is positioned so as to receive radiation via another of the first and second window/lens.

It may be desired to have one or more detector(s) directed in a particular direction, such as downwardly, and have a number of emitters positioned distributed over the assembly to emit radiation in different directions. Then, it may be desired to have the detector in the outer housing, as the orientation of this may be determined vis-à-vis an ear canal, and at least some of the emitters in or on other elements, such as the receiver, spout or dome.

One aspect of the invention relates to an assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing,
the sensor comprises a radiation emitter and a radiation detector,
the receiver housing and at least one of the emitter and the detector overlap at least partly when projected on to a first plane, and
the receiver housing and the at least one of the emitter and the detector overlap at least partly when projected on to a second plane perpendicular to the first plane.

Then, the assembly may further comprise an additional element, such as a spout or dome, attached directly or indirectly to the receiver, one of the emitter and the detector being attached to the additional element.

In one example:
the detector has a field of view having a first central axis,
the emitter defines an emission cone having a second central axis, where a non-zero angle exists between the first and second central axes.

The non-zero angle may be 1-5 degrees, 5-10 degrees, 7-20 degrees, 5-50 degrees, 10-80 degrees or the like. The axes may point toward each other or away from each other.

In one situation, the receiver housing has a number of at least substantially plane surface parts, wherein the detector is provided in or at a first of the surface parts and the emitter is provided in or at a second of the surface parts. Alternatively, at least one of the detectors/emitters may be positioned in or at an edge or corner thereof.

In one embodiment of the method, the method may further comprise a receiver having a receiver housing, wherein at least one of the one or more detectors and one or more emitters is attached to the receiver housing.

Then, an emitter may be positioned so as to emit radiation toward one of a first and a second window/lens and a detector is positioned so as to receive radiation via another of the first and second window/lens, the first window or lens being provided in or at the receiver housing and the second window or lens being positioned in or at either the housing or an element attached to the housing, An aspect of the invention relates to a method of providing an assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing, and
the sensor comprises a radiation emitter and a radiation detector,
the method comprising providing the receiver and the sensor so that:
the receiver housing and at least one of the emitter and the detector overlap at least partly when projected on to a first plane, and
the receiver housing and the at least one of the emitter and the detector overlap at least partly when projected on to a second plane perpendicular to the first plane.

The method then may further comprise an additional element attached to the receiver, one of the emitter and the detector being attached to the additional element.

Then:
the detector may receive radiation in a field of view having a first central axis, the emitter may output radiation in an emission cone having a second central axis, where a non-zero angle exists between the first and second central axes.

Also, the receiver housing may have a number of at least substantially plane surface parts, wherein the detector is provided in or at a first of the surface parts and the emitter is provided in or at a second of the surface parts.

In one situation, it may be desired to position the emitter(s) and detector(s) in a particular manner, where radiation may travel from the emitter to the detector through a too short path and thus create problems. Often, the problems are created by an overlap being provided between the field of view and the cone and being positioned in an undesired position, such as too close to the detector. In that situation, it may be desired to provide a radiation blocking element preventing this radiation.

Thus:
one of the radiation detectors is positioned in the housing and has a field of view,
one of the radiation emitters is positioned in the housing and has an emission cone,
the assembly further comprising a radiation blocking element provided in an overlap between the field of view and the cone.

A radiating blocking element may be positioned in an overlap between the field of view and the cone. Usually, the blocked overlap is a portion of the overlap which is close or the closest to the housing, the detector and/or the emitter. In that manner, radiation is prevented from travelling through that overlap and to the detector.

Clearly, alternatively, the field of view or cone may be adapted so as to not overlap at this position.

In one situation, the radiation blocking element engages the housing or is fixed to the housing (or forms part of the housing) and extends away from the housing. Naturally, the radiation blocking element may form part of any element of the assembly, such as a dome.

In one situation of the method:
one of the radiation detectors is positioned in the housing and receives radiation within a field of view,
one of the radiation emitters is positioned in the housing and emits radiation within an emission cone,
the method further comprising blocking radiation travelling in an overlap between the field of view and the cone.

Then, the blocking step may comprise blocking the radiation with a radiation blocking element engages the housing or is fixed to the housing (forms part of the housing) and extends away from the housing.

In one situation, the assembly further comprises a receiver, wherein:
the receiver comprises:
a receiver housing with a receiver housing wall part comprising a sound output,
a receiver diaphragm defining, with an inner surface of the receiver housing, a first chamber in the receiver housing,
one of the one or more detectors and one or more emitters comprises a sensor housing,
the receiver housing and the sensor housing overlap at least partly when projected on to a first plane, and
the receiver housing and sensor housing overlap at least partly when projected on to a second plane perpendicular to the first plane.

In another situation, the assembly further comprises a receiver, wherein:
the receiver comprises:
a receiver housing,
a receiver diaphragm defining, with an inner surface of the receiver housing, a first chamber in the receiver housing having a sound output, and a second chamber in the receiver housing,
one of the one or more detectors and one or more emitters comprises a sensor housing being at least partially inside the second chamber, and
the sensor housing or its portion inside the second chamber, having a volume not exceeding 20% of a volume of the second chamber.

An aspect of the invention relates to an assembly comprising a receiver and a sensor, wherein:
the receiver comprises:
a receiver housing,
a receiver diaphragm defining, with an inner surface of the receiver housing, a first chamber in the receiver housing having a sound output, and a second chamber in the receiver housing,
the sensor comprises a sensor housing being at least partially inside the second chamber, and
the sensor housing or its portion inside the second chamber, having a volume not exceeding 20% of a volume of the second chamber.

An aspect of the invention relates to an assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing,
the sensor comprises a sensor housing,
the receiver housing and sensor housing overlap at least partly when projected on to a first plane, and
the receiver housing and sensor housing overlap at least partly when projected on to a second plane perpendicular to the first plane.

In this context, the first plane may be a plane defined by the receiver diaphragm, but this is not required.

In this context, a housing will define an area or outer contour when projected on to a plane. An overlap thus is seen when the areas or contours of the two housings overlap.

When the two housings overlap in the two projections, the overall extent of the assembly may be made smaller, which has advantages, such as if it is desired to position the assembly inside the ear canal of a person.

In a first preferred embodiment, the sensor housing is positioned at least partly inside the receiver housing. Thus, the sensor housing may have an outer wall portion taking part in defining a chamber in the receiver housing.

When the sensor is positioned inside the receiver housing, it will affect the overall volume and thus the properties of the receiver. Thus, it may be desired that the sensor is rather small. In one embodiment, it is desired that the sensor housing has an outer volume not exceeding 20%, such as not exceeding 10% or even not exceeding 5%, of an inner volume of the receiver housing. Usually, the receiver has a front chamber, into which the sound outlet opens, and a second chamber on an opposite side of the diaphragm. In that situation, the sensor may be provided in the second chamber and take up no more than 20%, such as no more than 15%, such as no more than 10%, such as no more than 8% of a volume of the second chamber.

Naturally, the sensor housing may be positioned at least partly outside of the receiver housing.

The sensor housing may be attached to the receiver housing.

In one embodiment, the receiver diaphragm and sensor housing overlap at least partly when projected on to the first plane. In that situation, the receiver diaphragm need not be limited by the presence of the sensor which may extend in a chamber of the receiver, such as "under" the receiver diaphragm. The size of the diaphragm is a factor in the definition of the maximum sound intensity which the receiver may output, and it is usually desired to provide as large a diaphragm as practically possible.

In one embodiment, the receiver housing and sensor housing, when projected on to the first plane, overlap an area of at least 10%, such as at least 20%, such as at least 40%, such as at least 50%, such as at least 75%, such as at least 90%, such as 100% of an area of the sensor housing in the projection.

Alternatively or additionally, the receiver housing and sensor housing, when projected on to the plane perpendicular to the first plane, overlap an area of at least 10%, such as at least 20%, such as at least 40%, such as at least 50%, such as at least 75%, such as at least 90%, such as 100% of an area of the sensor housing in the projection.

Alternatively or additionally, the receiver diaphragm and sensor housing, when projected on to the first plane, overlap an area of at least 10%, such as at least 20%, such as at least 40%, such as at least 50%, such as at least 75%, such as at least 90%, of an area of the sensor housing In one situation, the sensor housing is box-shaped and has 6 outer wall portions, which are pair-wise parallel. Often, the sensor has rounded corners and edges. In this situation, the sensor housing may be selected so that a wall portion with a largest surface area has a surface area not exceeding two, such as not exceeding 1.8, such as not exceeding 1.5, such as not exceeding 1.3, times a surface area of a wall portion having the smallest surface area. In the situation where all wall portions have the same size would be the shape of a cube. In this context, the area of a wall portion may be that defined by the wall portion when projected on to a plane perpendicular to the wall portion or a portion of the wall portion.

In this situation, it is not desired to have e.g. a long and flat sensor housing, as the sensor housing, positioned in the receiver housing, may be exposed to very high sound pressures which may deform or vibrate too large wall parts of the sensor.

On the other hand, a certain inner volume is desired of the sensor housing, and thus, this more cube shaped shape is preferred as it allows the desired inner volume while keeping the wall parts relatively small.

In addition or alternatively, vibration of the sensor housing wall parts may be prevented by providing relatively stiff or thick walls of the sensor housing such as walls with a thickness of at least 0.5 mm, such as at least 0.75 mm, such as at least 1.0 mm, such as at least 1.5 mm, such as at least 2 mm, such as at least 2.5 mm, such as at least 3 mm.

The other of the emitter and the detector may be positioned outside of the receiver housing or, for example, at least partly in the first chamber of the receiver. Then, the portion of the emitter/detector inside the first chamber may have a volume not exceeding 20% of a volume of the first chamber.

Naturally, it may be desired to allow radiation to travel between the inner volume of the second chamber, such as if the emitter is provided fully within the second chamber, and the outside of the receiver housing to the tissue. In that situation, it is not desired to have sound passage along the same route, so a window, lens or the like may be provided in the receiver housing wall so as to allow radiation to pass but prevent sound from passing.

Actually, another interesting aspect is as that above where at least a portion of the emitter and/or the detector is positioned in the first chamber. Usually, the first chamber is more volume critical, but as emitters and detectors may be made extremely small, their presence in the first chamber would not be detrimental.

An aspect of the invention relates to an assembly comprising a receiver and a sensor, wherein:
  the receiver comprises:
    a receiver housing,
    a receiver diaphragm defining, with an inner surface of the receiver housing, a first chamber in the receiver housing having a sound output, and a second chamber in the receiver housing,
  the sensor comprises a radiation emitter and a radiation detector, one of the radiation emitter and the radiation detector being at least partially inside the second chamber.

Then, the portion of the one of the emitter and the detector inside the second chamber may have a volume not exceeding 20% of a volume of the second chamber.

In one situation, the method further comprises operating a receiver, comprising:
  a receiver housing with a receiver housing wall part comprising a sound output,
  a receiver diaphragm defining, with an inner surface of the receiver housing, a first chamber in the receiver housing,
the method comprising providing the housing, a sensor with a sensor housing and the receiver so that:
  the receiver housing and a sensor housing overlap at least partly when projected on to a first plane, and
  the receiver housing and sensor housing overlap at least partly when projected on to a second plane perpendicular to the first plane.

In another embodiment, the method further comprises operating a receiver comprising:
  a receiver housing,
  a receiver diaphragm defining, with an inner surface of the receiver housing, a first chamber in the receiver housing having a sound output, and a second chamber in the receiver housing,
the method comprising providing the housing, a sensor with a sensor housing and the receiver so that:
  one of the one or more detectors and one or more emitters comprises a sensor housing being at least partially inside the second chamber, and
  the sensor housing or its portion inside the second chamber, having a volume not exceeding 20% of a volume of the second chamber.

An aspect of the invention relates to a method of providing an assembly of a receiver and a sensor, wherein:
  the receiver comprises:
    a receiver housing,
    a receiver diaphragm defining, with an inner surface of the receiver housing, a first chamber in the receiver housing having a sound output, and a second chamber in the receiver housing, and
  the sensor comprises a sensor housing being at least partially inside the second chamber, the method comprising providing the sensor housing or its portion inside the second chamber, having a volume not exceeding 20% of a volume of the second chamber.

An aspect of the invention relates to a method of providing an assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing,
the sensor comprises a sensor housing,
the method comprising providing the receiver and sensor so that:
the receiver housing and sensor housing overlap at least partly when projected on to a first plane, and
the receiver housing and sensor housing overlap at least partly when projected on to a second plane perpendicular to the first plane.

Then, the sensor housing may be positioned at least partly inside the receiver housing.

The sensor housing may have an outer volume not exceeding 20% of an inner volume of the receiver housing.

The sensor housing may be box-shaped and have 6 outer wall portions, where a wall portion with a largest surface area has a surface area not exceeding twice a surface area of a wall portion having the smallest surface area.

The sensor housing may be positioned at least partly outside of the receiver housing.

The sensor housing may be attached to the receiver housing.

The method may further comprise one or more conductors connected to the sensor housing and extending outside of the sensor housing, at least a part of the conductor(s) extending inside the receiver housing.

The receiver diaphragm and sensor housing may overlap at least partly when projected on to a first plane.

The receiver housing and sensor housing, when projected on to a first plane, may overlap an area of at least 10% of an area of the sensor housing in the projection.

An aspect of the invention relates to a method comprising providing an assembly of a receiver and a sensor, wherein:
the receiver comprises:
a receiver housing,
a receiver diaphragm defining, with an inner surface of the receiver housing, a first chamber in the receiver housing having a sound output, and a second chamber in the receiver housing,
the sensor comprises a radiation emitter and a radiation detector, one of the radiation emitter and the radiation detector being at least partially inside the second chamber.

Then, the portion of the one of the emitter and the detector inside the second chamber may have a volume not exceeding 20% of a volume of the second chamber.

It may be desired to provide a symmetrical design so that the same assembly may be used in both the left and the right ear canal of a person. In this case, it may be desired to have one lay-out of the detectors/emitters in one ear canal and a mirrored set-up in the other canal. Providing both set-ups in an assembly arrives at a symmetric design.

Preferably the mirroring is performed via a vertical plane.

In one situation:
the radiation detector(s) are positioned in or symmetrically on either side of a plane extending through the housing and/or
the radiation emitter(s) is/are positioned in or symmetrically on either side of the plane.

In this context, symmetrical on either side means that one emitter/detector is mirrored into another one via the plane. In this context, mirroring means representing the element on the opposite of the plane perpendicularly on the plane and in the same distance from the plane.

In one situation, the housing is configured to be positioned so that the plane is at least substantially vertical such as when the housing is positioned in the ear canal of a person standing up and looking straight ahead.

Symmetry may be obtained in two manners: providing two elements, one on either side, or providing one element positioned in the plane or extending equally on either side of the plane.

In one situation, at least one detector is positioned to receive radiation travelling in the plane.

It may be desired to provide detector(s) only in the plane and emitters on either side of the plane.

In one situation, the method comprises:
positioning the radiation detector(s) in or symmetrically on either side of a plane extending through the housing and/or
positioning the radiation emitter(s) in or symmetrically on either side of the plane.

The housing may be positioned in an ear canal so that the plane is at least substantially vertical.

At least one detector may be positioned to receive radiation travelling in the plane.

The method may comprise providing two of the assemblies and providing one in a left ear canal of a person and the other in the right ear canal of the person.

Clearly, the operation of the sensors of one assembly may be adapted according to which ear canal it is provided in. Thus, the operation of the assemblies may differ from left to right side. Usually, this difference will relate to mirrored operation, so that, for example, if the right side emitter(s) are operated in the left ear canal, the left side emitter(s) may be operated in the right ear canal.

Thus, the assemblies may be programmed according to which side they are provided in.

Also, if sensors are provided in both assemblies, the sensor in only one assembly need be operated at the time, such as to save energy. The sensor of the other assembly may occasionally or periodically make a measurement to compare the quality to the operating sensor of the other assembly. If that measurement quality is better, the operation may shift to the other assembly. Operation may also shift if the operating assembly is low on power.

Thus, the method may comprise feeding information e.g. from a processor in a BTE or from a processor in an earphone or a mobile telephone to an assembly as to whether the assembly is (to be) used in a right ear of a left ear. Then, the sensor of the assembly may, based on that information, operate some emitters/detectors and not others. Clearly, if the assembly was informed that it was to be used in the other ear, it may operate other emitters/detectors. In the above situation where the assemblies have mirrored detectors/emitters, one of a mirrored pair may be operated in the left ear and the other of the pair in the right ear.

The method further may comprise evaluating, between two assemblies, such as when used in the ear canals of a person, which assembly has the best signal quality from the optical sensor(s) and the rendering of the optical sensor of the other assembly inactive. Clearly, the inactive sensor may still perform some sensing in order for its signal quality to be known so that it may be rendered active (and the presently active sensor may then be rendered inactive), if its signal quality increases or surpasses that of the presently active sensor (in the other ear).

In another embodiment, both assemblies in both earcanals may be intentionally activated, for example, if certain redundancy is required in the sensing, or for example, if sensing from both ear canals will improve the quality of the processing by a processor. It has been found preferable to provide at least most of the detectors and/or emitters rather close to the portion of the housing which is the farthest into the ear canal or closest to the ear drum.

Usually, the housing is configured to also output sound toward the inner ear. Thus, the housing has a sound output. Clearly, the housing may then comprise a receiver or may have an input for receiving sound from a sound generator not provided in the housing, such as provided in a BTE portion connected to the housing.

In one situation, the housing is oblong with a first end portion and a second, opposite end portion, the housing comprising a sound outlet in or at the first end portion, where a majority of the radiation emitter(s) and a majority of the radiation detector(s) is/are positioned closer to the first end portion than the second end portion.

The position of an emitter may be that of a centre of the emitting portion of the emitter.

The position of a detector may be a centre of a sensitive portion thereof.

The positions may be determined in a projection of the emitters and detectors on a longitudinal axis, such as a symmetry axis, of the housing.

The housing may comprise a spout through which sound is output. This spout may not be seen as a part of the housing.

The housing may have a symmetrical shape with the first and second end portions being mirrored in a plane perpendicular to the longitudinal axis.

In one situation, the assembly further comprises a receiver positioned in the housing, where a majority of the radiation emitters and the radiation detectors are positioned, in a projection on to a longitudinal axis of the housing, closer to the first end portion than a centre of the receiver.

The majority may be 50% or more, such as 60% or more, such as 75% or more.

A dome may be provided for attaching the housing in and ear canal. Often, the dome is attached in the front or inner portions of the housing and thus where the emitter(s) and detector(s) are desired. Then, the dome or portions thereof may be transparent or translucent to the radiation, or be made such that they guide the radiation to wanted positions, or block them from reaching unwanted positions.

In one embodiment of the method, the housing is oblong with a first end portion and a second, opposite end portion, the housing comprising a sound outlet in or at the first end portion, the method comprising positioning a majority of the radiation emitter(s) and a majority of the radiation detector(s) closer to the first end portion than the second end portion.

In another embodiment, the method comprises a step of positioning a receiver in the housing, where the step of positioning the majority of the radiation detector(s) and the majority of the radiation emitter(s) comprises positioning a majority of the radiation emitters and the radiation detectors are positioned, in a projection on to a longitudinal axis of the housing, closer to the first end portion than a centre of the receiver.

Another aspect of the invention relates to an assembly of a receiver, a radiation emitter, a radiation detector and an assembly housing, wherein:
the receiver has a receiver housing and is positioned inside the assembly housing,
the radiation detector is positioned in the assembly housing and has a reception direction along a first direction,
the radiation emitter is positioned in the assembly housing and has an emission direction along a second direction,
an angle existing between the first and second directions,
one or more windows transparent to the radiation are provided in the assembly housing for allowing radiation from the emitter to exit the assembly housing and radiation from outside of the assembly housing to reach the detector.

In this context, a radiation emitter and a radiation detector may be as described above. As mentioned, the radiation wavelength may be selected depending on the parameter sought detected. Wavelength selection may be made by selecting the emitter and/or by employing filters.

A radiation emitter will emit radiation in a cone, as described above, inside which an emission direction may be defined, usually in the direction receiving the highest intensity of radiation and/or a symmetry axis of the emitter.

Also, the detector will have a reception characteristic defining a main direction, such as a symmetry axis of the reception pattern A window is transparent to the wavelength in question, if it absorbs, reflects or scatters no more than 50% of the radiation at that wavelength when launched perpendicularly through the window. Usually, a much lower absorption/scattering/reflection, such as no more than 30%, 20%, 10%, 5% or less is desired.

The assembly housing may be configured to be positioned within an ear or ear canal of a person. The assembly may be a hearing aid or a hearable, or a part thereof. The assembly may comprise also other elements, such as batteries, microphones, processors or the like. Alternatively, such components may be provided in other elements connected to the present assembly, as in the situation where hearing aid has an In The Ear (ITE) portion forming the assembly and a Behind The Ear (BTE) portion connected to the ITE and having for example the battery.

The emitter or detector may be provided in the receiver housing or in a cut-away thereof as described above in relation to the overlapping fashion. Alternatively, both the emitter and the detector may be positioned outside of the receiver housing. The emitter/detector may be attached to the outer side of the receiver housing and/or to e.g. an inner surface of the assembly housing.

The directions have an angle to each other. When the directions are directly opposite to each other, the angle is 180 degrees.

If the angle is zero (the directions are parallel), a predefined minimum distance may be desired between the two directions in order to ensure that radiation passes from the emitter to the detector, via the surroundings of the assembly housing, via a route of at least another minimum distance.

When the angle is non-zero, the directions may be pointed toward each other to form an overlap, if desired, between the cone and the field of view. Alternatively, the directions may be selected so that no overlap is seen.

In some situations, it may be desired to have the directions perpendicular to each other, such as between 20 and 50 degrees or between 45 and 135 degrees, such as between 60 and 120 degrees. It may alternatively be desired to have the directions opposite to each other, so that the angle is around 180 degrees, such as between 150 and 210 degrees.

If the assembly housing has 6 rather straight sides (may have rounded corners/edges) perpendicular to each other, it may be desired that the directions each are at least substantially perpendicular to a side. In this manner, the emitter/detector may be attached to a side or in relation thereto.

In one situation, a number of radiation emitters are provided. These may be positioned in a variety of manners, such as with different emission directions. It may be desired that the emitters emit radiation in different directions so as to emit radiation into as large a portion of the surroundings, such as an ear canal, as possible. In one situation, the emitters are positioned in a single plane and with different directions within that plane. In other situations, one emitter may have a direction perpendicular to that of another emitter.

In addition or alternatively, multiple detectors may be provided so as to e.g. be able to collect radiation from as large a portion of the surroundings as possible. In one situation, the detectors are positioned in a single plane and with directions within that plane. In other situations, one detector may have a direction perpendicular to that of another detector.

In one situation, the receiver has therein a membrane provided in a membrane plane. In this situation, it may be desired that a direction of an emitter and/or a detector is provided at least substantially in the membrane plane, perpendicular or parallel thereto. Alternatively, the angle between the emitter and/or detector direction and the plane may be 5-85 degrees, such as 10-30 degrees, 20-40 degrees, 30-50 degrees, 40-60 degrees, 50-70 degrees, or 60-80 degrees. Clearly, an emitter may have one angle to the plane and a detector another angle. Also, the emitter direction and detector direction may, when projected on to the plane, have different angles between them.

In one situation, it is desired to have the radiation interact with the tissue positioned vertically and below the assembly housing. Thus, it may be desired that an emitter and/or a detector has its direction at least substantially vertical, when positioned in the ear canal of a person standing up. For example, this direction may be no more than 40 degrees, such as no more than 30 degrees, such as no more than 20 degrees, such as no more than 10 degrees from vertical.

Certain portions of ear canal may be more favourable to measure the physiological signals than other areas. For example, areas closer to eardrum may be preferred, or bottom area. In one embodiment, it is desired to avoid certain areas of ear canal, for example, areas of ear canal where there is a lot of motion due to physical activities of a person which cause body volumes close to certain parts of ear canal to move and hence create distortions that result in inferior measurements of physiological signals. The emitter or detector may be positioned in the hearing device such as to avoid such undesirable areas. Alternatively, the whole hearing device may be moved, e.g. shifted longitudinally or rotated in ear canal, to change the area of interaction of detector or emitter with ear canal.

Thus, the method may comprise the step of determining relative movement between an ear canal and the assembly housing and operating in accordance with the relative movement determined.

Relative movement may be determined using an accelerometer. This type of sensor will describe e.g. that the person is moving, such as running. This may displace the housing in the ear canal and may affect the optical measurement.

Another cause for relative movement is when the person speaks. In this situation, portions of the ear canal may deform causing relative movement of the portions with respect to the assembly housing, even though the housing may itself be more or less stationary with respect to the person's body. Thus, the determining step may comprise determining speech. A voice pickup sensor may be used for determining speech. A voice pickup may determine speech from sound or vibrations transported in the head of the person. When the speech, for example, exceeds a threshold limit, relative movement may be assumed or determined.

Yet another manner of determining relative movement is from the output of the optical sensor itself. E.g. a PPG signal will vary when relative movement takes place, so the movement may be determined from the PPG signal.

The action taken when relative movement is determined may be to control the hearing device to prompt a user or operator to alter the position or rotation of the housing in the ear canal. Thus, the reaction to the relative movement may be a displacement of the housing along the longitudinal direction of the ear canal. Alternatively or additionally, the reaction may be a rotation of the housing in the ear canal.

This prompting may be provided to the user via a receiver, if present, provided in the assembly housing. The assembly may be configured to output such a prompt when the movement is determined.

Other reactions could be to select particular emitter(s) or detector(s) when relative movement is seen. In one embodiment, a downwardly (vertical) detector may be selected.

Yet another reaction could be to search for useful sets of one or more emitter and one or more detector by simply activating different such sets of emitter(s) and detector(s) and determining a set with a sufficient signal quality.

Numerous manners exist of ascertaining that the assembly is positioned correctly in the ear canal of a person. In one situation, the assembly may have an indication enabling an operator to orient the assembly correctly during insertion. In another situation, the assembly may have multiple emitters and/or detectors with different directions, so that the emitter and/or detector with the lowest angle to vertical and downward may be selected or operated.

In the first situation, the window(s) of the assembly housing may assist the operator in determining how to orient the assembly during insertion. In other examples, the assembly housing may be fitted to the ear canal so that the orientation is defined by the shape. Otherwise, the housing may have a visible indication, such as an arrow. Alternatively, a cable attached to the assembly housing may have an indication or be fastened in a particular manner to the housing indicating to the operator how to orient the assembly housing. Actually, the cable may be used for rotating the assembly while positioned within the ear canal.

As to the second situation, this may employ a sensor, such as an accelerometer, to this effect. In one situation, multiple emitters and/or detectors may be positioned with different angles to a horizontal plane. These may be positioned in a plane perpendicular to a horizontal direction, such as around a longitudinal direction or axis of the housing. Preferably, the axes are distributed in relation to the horizontal plane, such as at a more or less defined angular spacing, so that one will have a lower angle to vertical than others. Often, the assembly housing has a sound output for receiving sound from the receiver and for outputting this sound to the surroundings. As mentioned, the assembly housing may be shaped to or configured to be positioned in the ear canal of a person. In that situation, the sound output would be directed toward the inner ear and the ear drum. The assembly housing may comprise a spout or the like defining the sound output.

In such situations, it is preferred that the radiation interferes with the tissue close to the sound output or even closer to the ear drum.

Thus, in some embodiments, the radiation emitter and/or the detector is directed at an angle below 90 degrees to a direction of the sound outlet, such as the direction of sound emitted from the sound outlet. If the sound outlet is in the shape of a spout, this will normally be a symmetric element, where the symmetry axis may be the direction of the sound outlet.

The sound outlet may also have the shape of an opening in a plane surface. In that situation, the direction of the sound outlet may be a symmetry axis of the opening, such as if drilled or punched-out. Alternatively, the direction may be perpendicular to the surface having the sound outlet.

When the angle is below 90 degrees, radiation is launched more in the direction of the sound outlet than in the opposite direction and/or radiation is detected from that direction.

Naturally, the angle may be as low as possible, such as below 80 degrees, below 70 degrees, below 60 degrees, such as below 50 degrees or 45 degrees or even 30 or 20 degrees. The angle may be 10-80 degrees, such as 11-70 degrees, such as 12-60 degrees, such as 15-50 degrees.

In that or another situation, the windows in the assembly housing for transmitting the radiation may also be positioned close to the sound output. The windows preferably are positioned closer to the sound output than to an opposite end of the assembly housing. If the sound outlet is in the form of a spout, it may be desired to provide the windows in the spout. Alternatively, as the spout may be used for attaching the housing to e.g. a dome, it may be desired that the windows are not in the spout but close to the spout, such as closer to the spout than to an opposite end of the assembly housing.

The assembly housing may have a generally longer dimension, which may be the longest Euclidian distance between any portions of the assembly housing. Then, at least one of the windows may be positioned no more than 40%, such as no more than 30%, such as no more than 20% of the longest dimension from the sound outlet or the base of the spout if present.

In general, multiple detectors or multiple emitters may be used. Often, multiple detectors would be positioned at different positions around the receiver housing so as to receive radiation from different directions. It may be desired that the detectors do not have overlapping fields of view so as to increase the tissue volume from which radiation may be received.

In one embodiment, a controller is provided for receiving the output of the detector(s) and for feeding the emitter(s). Naturally, multiple controllers may be used. A controller may be any type of processor, DSP, ASIC, monolithic or formed by a number of such elements.

In one situation, the controller is positioned in the receiver housing. Then, if the emitter(s) and/or detector(s) is/are not provided in the receiver housing, the controller may be connected to the emitter(s)/detector(s) via electrically conducting vias in the receiver housing. Such vias or connections may also be used for outputting a signal from the controller to e.g. an external unit receiving this signal. The controller may determine e.g. the pulse or the like from the outputs of the detectors and thus output information indicating this pulse or the like, or the controller may output information derived from the signals from the detectors, so that the final analysis may be made by an element, such as another controller, receiving the output of this controller.

Thus, a controller may be provided in the receiver housing and electrical connections be provided from the controller through the receiver housing to the emitter(s) and/or the detector(s). Also, electrical connections may be provided through the receiver housing wall for powering the controller and/or for transferring instructions or data to or from the controller.

The controller can be provided in the RIC housing for example, on the same PCB as the PPG components.

The controller can be positioned also in a connector attached to RIC, such as described in for example EP3343952 or EP3116240.

In yet another embodiment, the controller may be attached to a detector or emitter.

The assembly may further comprise one or more conductors connected to the sensor housing, such as the above electrically conducting elements, in order to e.g. receive a signal. Such conductors will then extend outside of the sensor housing but will preferably extend, at least for a portion of a length thereof, inside the receiver housing, such as to electrically conducting elements on or at an outer surface of the receiver housing so that the signal from the sensor may be delivered to such conducting elements, via the conductors. Then, the conductors may be at least partly protected by extending inside the receiver housing. In one situation, the electrically conducing elements of the sensor may be provided in a wall portion of the sensor housing facing a wall portion of the receiver housing. This portion of the receiver housing may comprise, as a portion of the conductors, electrically conducting elements to which the conducting elements of the sensor housing are connected.

In this context, the conductors may extend within the inner volume of the housing or e.g. within the housing walls thereof.

In that situation, the connections for both the receiver and the sensor may be made to the receiver housing. The electrically conducting elements for these connections may be provided in the same wall portion of the receiver housing, such as a wall portion opposite to a wall portion in which the sound output is provided.

Naturally, alternatively, the conductors for the sensor may simply extend around the receiver housing and away therefrom.

All (or part of) components can be mounted in (flex)PCB and then selectively attached to outer housing.

In general, when multiple detectors are provided, it is possible to monitor the output of the detectors and/or combine the output thereof. For example, if the ear canal changes shape or the housing changes position in the ear canal, one detector may receive an increased signal and another detector may receive a reduced signal. This may be the situation if the detectors are positioned so that one moves closer to the tissue by the movement and the other moves farther away from the tissue by the movement (if the two detectors are positioned oppositely on the housing). Thus, adding the two signals may arrive at a combined signal which is more independent of this movement. of course signals from any multiple of detectors/emitters can be combined (with any mathematical operation) to improve the PPG signal and to reduce and (movement induced) noise e.g. by compensation.

In the following, preferred embodiments of the invention will be described with reference to the drawings:

FIG. 3 illustrates a receiver with multiple detectors,

FIG. 4 illustrates how to launch radiation through the receiver wall,

FIG. 5 illustrates a receiver with a large emitter/detector at the far end,

FIG. 6 illustrates the many possibilities of directions of the emitter and detector, FIG. 7 illustrates an assembly housing having windows for radiation to pass and FIG. 8 illustrates a receiver with a controller.

Figure 1:
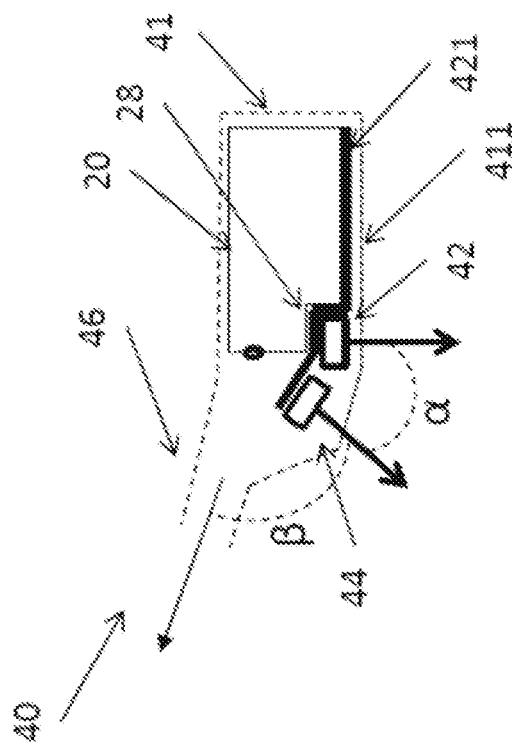
FIG. 1 illustrates an embodiment of an assembly with an optical sensor.

In FIG. 1, an assembly of a receiver with a receiver housing 20, an outer housing 41 attaching the receiver housing 20 to a spout 46 and a radiation emitter 44. In a recess of the receiver housing, a light receiver or detector 42 is provided.

The receiver housing 20 has a lower indentation or cavity 28 in which the detector 42 is positioned.

Numerous alternatives exist. The cut-out in the receiver housing 20 may be made large enough to accommodate both the emitter and the detector. Also, the emitter/receiver received in the recess may instead be provided fully within the receiver housing 20 or partly therein so as to e.g. protrude from the receiver housing.

A flexible PCB 421 is illustrated extending from the right end of the receiver housing 20, below the receiver housing and between the receiver housing and the detector and the emitter, respectively. This PCB provides the electrical contacting to the receiver and detector. Contacting to the receiver housing could take place at the right side thereof, so that all elements may be contacted at the same side of the receiver.

It is noted that the flexible PCB 421 of FIG. 1 may be useful also in a more general setting, as it may also be suitable for use in the receiver housing, when the detector/emitter is fully or partly provided therein. The motor could also be connected to this flexible PCB.

This embodiment may be rather simply assembled, as the emitter and detector may be attached to the flexible PCB and may then be forced into the desired position by the outer housing 41.

The portion 411 of the housing 411 is made transparent to the radiation output by the radiation emitter 44.

It is seen that an angle, α, is provided between the symmetry axis (arrows) or centre of the line or cone of sight of the detector and emitter. Thus, radiation has to pass a distance from the emitter before reaching tissue from which it may be reflected to the detector.

Also, the direction of the spout 46 is indicated as well as an angle, β, between the axis of the emitter 44 and the direction of the spout. It may be desired at β is less than 90 degrees for the detector and/or the emitter.

As mentioned above, the light preferably travels at least a minimum distance in the tissue from the emitter to the detector. The light or radiation may thus be reflected/scattered more than once and may therefore travel around corners. Therefore, the emitter and detector need not be positioned on or at the same side (as illustrated in FIG. 1) of the receiver housing 20. In fact, the emitter and receiver may be desired positioned on different sides, such as one at the top and one on the left, right, back, front or the lower side of the receiver housing 20.

Figure 2:
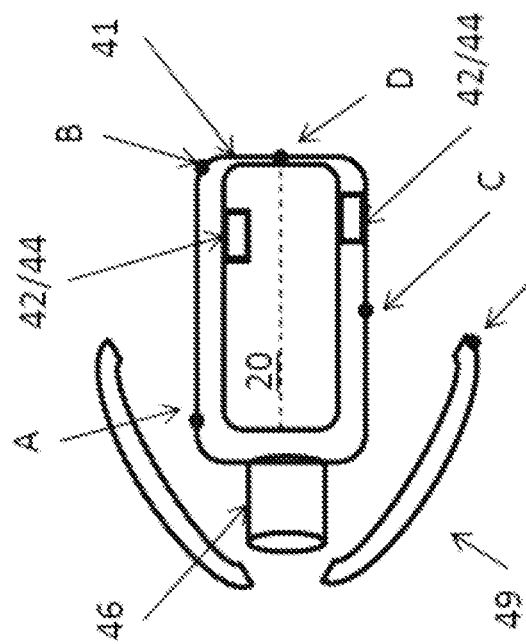
FIG. 2 illustrates a receiver connected to a dome and having an optical sensor.

In FIG. 2, a receiver 20 is placed in a receiver assembly housing 41 which is, in turn, also accommodating a spout (nozzle) 46 connected to a dome 49. The receiver may, naturally, be connected to a number of other elements or within other housings.

In this figure, four exemplary positions, A, B, C, D and E are illustrated. One or more of these may be used for the emitter and one or more of the remaining ones may be used for the detector.

Figure 11:
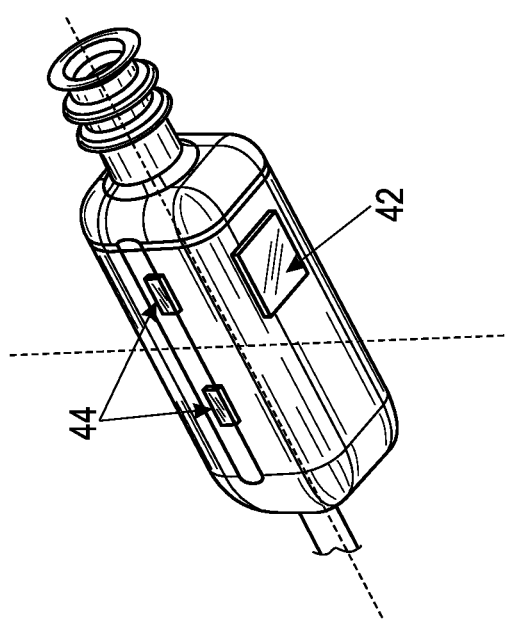
FIGS. 9-12 illustrate a symmetrical set-up with emission cones and field of view.
Figure 12:
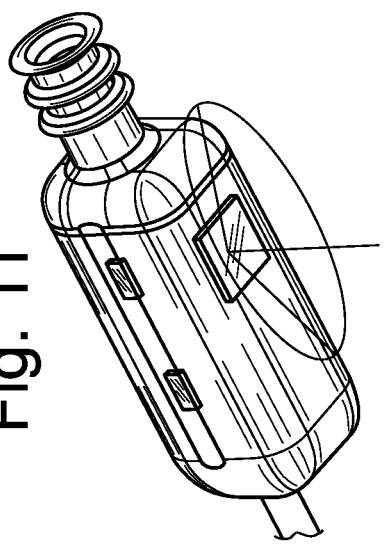
Figure 9:
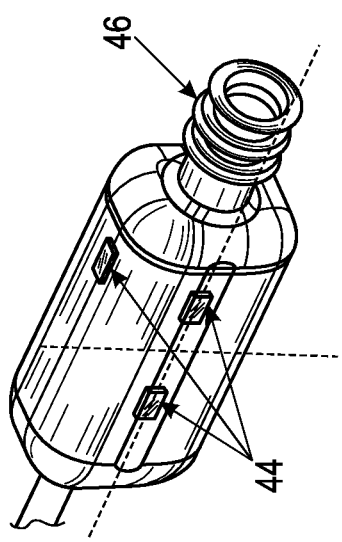
Figure 10:
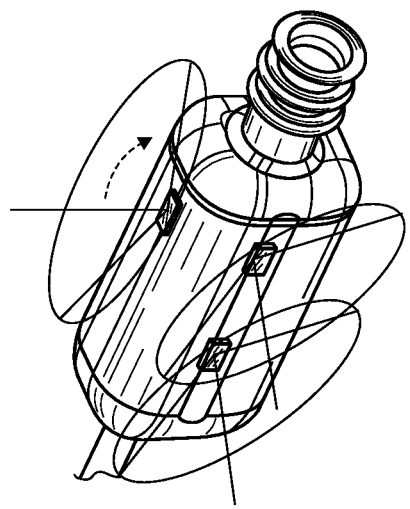

In FIGS. 9-12, a receiver housing or outer housing is illustrated having emitters 44 positioned along the sides thereof as well as on the top (in the direction illustrated in FIG. 9) as well as a detector 42 in the bottom. In FIGS. 10 and 11 the emission cones and field of view are illustrated, where the emission cones and field of view may be defined as FWHM angles, for example.

Figure 13:
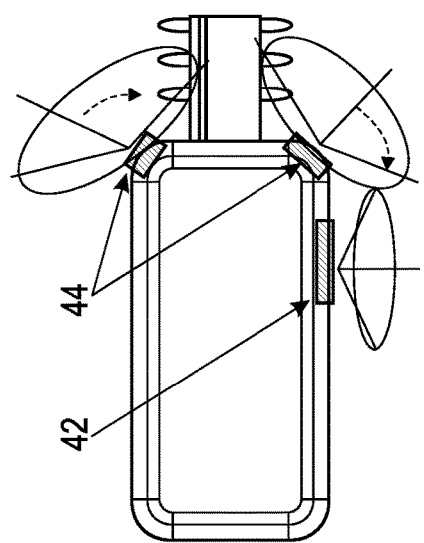
FIG. 13 illustrates emitters or detectors also at corners of a housing.

In FIG. 13, alternative positions are indicated, which may be not only on or at the plane sides but also at corners or edges.

Preferably, the emitters 44 are positioned symmetrically around or in a vertical symmetry plane of the housing. In that situation, the same housing may e.g. be used in any ear canal of a person. Preferably, at least one emitter or detector is directed directly downwardly or upwardly, as signals to/from a vertical direction are interesting.

Naturally, if the detector(s) and/or emitter(s) is/are positioned in the receiver housing, the receiver may be directed, vis-à-vis the outer housing so that they have the desired directions relative to vertical when the outer housing is inserted in an ear canal. Ear canals may be oval and so may the outer housing. However, as the oval shape is not necessarily directed, vis-à-vis vertical, identically in all persons, the outer housing may be rotated differently vis-à-vis vertical. This rotation may be counter-acted by rotating the receiver housing inside the outer housing.

Clearly, in this situation, sufficiently large windows/lenses may be provided in the outer housing in order to allow for such rotation without unnecessary blocking of the radiation.

Figure 14:
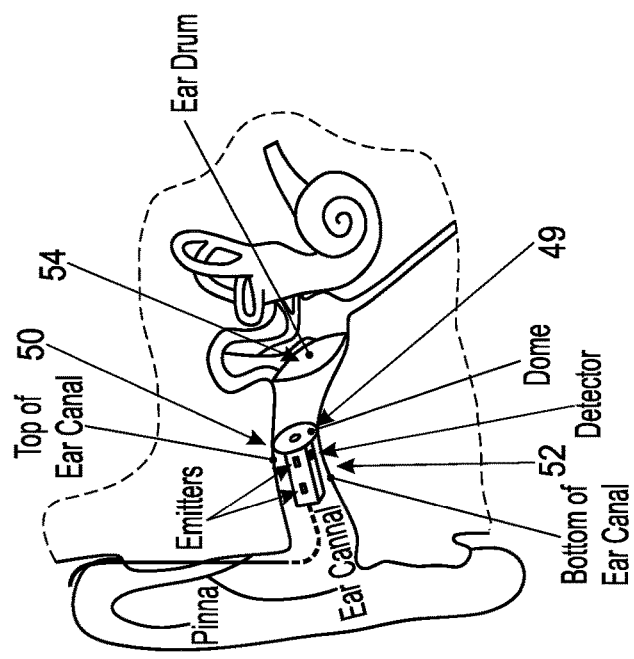
FIG. 14 illustrates a housing in an ear canal.

In FIG. 14, the outer housing with the dome is illustrated inside an ear canal with an ear canal top 50, an ear canal bottom 52 where a dome 49 is provided proximate the ear drum 54.

Clearly, an emitter or detector may be provided inside the receiver housing and/or outside of the receiver housing but still in the assembly housing 41.

As embodiments exist in which no receiver is present at all, the positions in/on the receiver are not essential. Clearly, the present invention is targeting an in-the-ear-canal position of optical measurement. Very often, it is desired to provide sound also in the ear canal, a receiver is an obvious choice. However, a receiver may also be positioned in other positions and a sound guide be provided to and usually through the housing 41 to an output thereof—such as the spout 46.

In FIG. 3, a receiver is illustrated having an upwardly directed emitter 44 provided in the first chamber and two detectors 42 positioned in the second chamber. This merely illustrates that multiple emitters and/or detectors may be used, and that these may be positioned in different positions completely within, partly within or outside of the receiver housing.

When multiple detectors are used, it is preferred that they have non-overlapping fields of view, such as when directed in different directions. In FIG. 3, the two detectors look in different directions (one is directed downwardly and one to the side) and do not overlap Providing multiple detectors increases the volume of the tissue from which radiation can be received.

In the same manner, multiple emitters may be used in order to provide radiation to a larger tissue volume. Again, this may increase the overall volume from which radiation may be received. In FIG. 3, an additional emitter 44 pointing downwardly is illustrated.

As mentioned above, it may be desired to ensure that the radiation travels at least a predetermined distance in the tissue before reaching the detector. This may be ensured by tailoring the fields of view of the emitter (could also be called emission cone) and detector so that radiation has to move from one emission cone to the other and then to the detector. Alternatively, a blocking element, as that illustrated at 43, may be provided which blocks a portion of a field of view of one of the detector and emitter—or both—so as to again force the radiation to travel further before reaching the detector. In FIG. 3, a narrow emission cone is illustrated in unbroken lines and a wider, partly blocked, emission cone is illustrated in dashed lines.

In FIG. 4, different embodiments are seen when the detector 42 or the emitter 44 is provided in the receiver housing 20. In this situation, a window 50 may be provided for allowing radiation to pass from inside to outside of the housing wall (or vice versa). Also, a mirror 45, or other optics, or an optical fibre 47 may be provided for guiding the radiation to/from the emitter/detector from/to the window 50. The window 50 may have a particular shape and/or be replaced by a lens or the like in order to adapt the field of view if desired.

In FIG. 5, an embodiment of a receiver 20 is seen comprising a diaphragm 24 and a motor 27. Also provided in the receiver housing 20 is a radiation emitter 42 or a detector 44 which in this example extends from below to above the plane of the diaphragm which therefore in that is made smaller. The advantage of providing the emitter/detector in the far end of the housing 20, compared to the sound output 23, has the advantage that the diaphragm is usually driven by the motor at a position rather close to the output—compared to the situation where the output was provided at the end of the emitter/detector. The point of driving the diaphragm usually has the largest deflection of the diaphragm, and the closer this position is to the output, the larger sound intensity can be output.

FIG. 6 illustrates the receiver housing 20 or the assembly housing 41 and a number of the directions which could be used for emitters and/or detectors. No boundaries really exist as to which directions to use.

In FIG. 7, a receiver housing 20 or an assembly housing 41 is illustrated having two windows directed at 90 degrees to each other.

When the windows are also visible in the assembly housing, the orientation of the assembly housing may be ascertained or corrected. This may be the situation where a particular direction is desired of the radiation emitted or received and/or where it is desired that the radiation has interacted with tissue with a particular position vis-à-vis the assembly or within the ear canal. In particular, as described above, it may be desired that the tissue is that directly below, vertically, the assembly, especially when the person is standing up. Then, the positions of the windows may be used by the operator when inserting the assembly so that the window is pointed downwardly, so that the radiation emitted through the window or received through the window is to or from that direction.

Actually, the ear canal of a normal person has an oval cross section. Thus, when the housing 41 has a corresponding oval shape, the direction of the radiation output and of the field of view of the detector(s) may be rather simply controlled by controlling the direction of the optical elements in relation to the housing 41. Often, however, the outer housing has a shape corresponding to that of the receiver, i.e. slightly oblong with a quadratic cross section perpendicular to the longitudinal axis and with rounded corners.

In the situation where the emitter(s) and detector(s) are attached to or in the receiver housing, this may simply be obtained by orienting the receiver housing within the outer housing. Receivers often are at least slightly oblong with a quadratic cross section perpendicular to their longitudinal axis (see FIG. 7), where the cross section is oblong and not squared (and has rounded corners). This oblong cross section thus facilitates orienting the receiver housing correctly in the outer housing.

A slightly complicating factor is that the ear canal shape is not the same from person to person so that the longest dimension in the oval cross section will not necessarily have the same angle to vertical for all persons. Thus, the orientation vis-à-vis vertical of an outer housing with an oval cross section may differ from person to person. Then, so may the orientation of the receiver housing within such outer housings and/or the emitter(s) and detector(s) if not attached to the receiver housing.

In case the oval cross section of an ear canal is too rotated, the desired directions of the radiation may be obtained by attaching the detector(s)/emitter(s) at an angle to the receiver housing, such as in corners/edges thereof.

Naturally, the shape of the outer housing need not correspond entirely to that of the ear canal. The outer housing may be made smaller and be attached in the ear canal using e.g. a dome.

Often, however, an outer housing may be designed which may be used in both ear canals of a person. Then, manufacture will be easier, as two hearing aids for that person may be made from a single process or a single mold.

In one embodiment, however, the outer housing is made especially to the particular ear canal, so that the definition and manufacture of the housing may include the positioning and building-in or including of any windows or the like.

It may also or alternatively be desired to provide the emitters and detectors or at least a majority thereof close to the ear drum, such as in the portion of the receiver and/or outer housing which is the closest to the ear drum.

As indicated in FIGS. 9-12, most of the emitters and detector(s) are positioned in that half of the housing which is closest to the spout 46. Usually, the spout or sound output is directed toward the inner ear.

Figure 16:
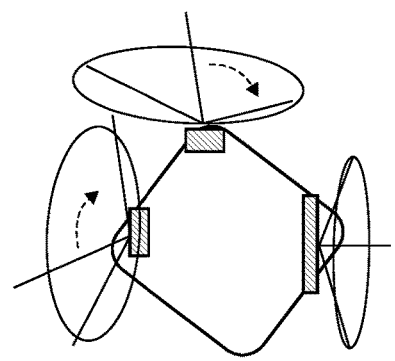
FIGS. 15 and 16 illustrate embodiments with no overlap between the fields of view and the cones.
Figure 15:
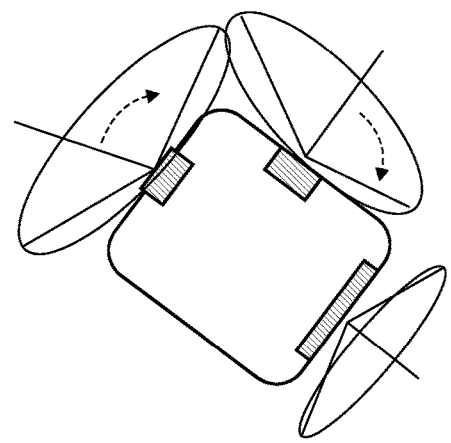

FIGS. 15 and 16 illustrate different embodiments where there is no overlap between the fields of view and cones. It is seen that the positions of the detectors and emitters may be selected for a number of purposes, one being no overlap and others being the desired direction(s) to output radiation to or receive radiation from.

These assemblies may be used in different situations, such as depending on the angle between vertical and the longest dimension of the ovality of the ear canal. If this longest dimension is rotated sufficiently far, it may be desired to provide the emitters/detectors in the edges/corners (FIG. 16) in order to have the emission and detection from the desired directions (often downwardly). An alternative would be to rotate the receiver housing in the ITE housing, but this is often not possible, as the receiver housing exterior shape and the ITE housing interior shape do not often allow a sufficiently large rotation of the receiver housing when provided in the ITE housing. Then, a solution would be so use a receiver housing with the alternative positions of the detectors/emitters.

Normally, the cable connecting the ITE and the BTE parts of the hearing instrument keeps the device in the optimal orientation/position.

The housing may be fastened in the ear canal using a dome, double dome, custom dome, custom mould, sportslock or the like.

FIG. 8 illustrates an embodiment where the receiver 20 is provided in the assembly housing 41 but neither of the emitter or detector is provided in or at the receiver. The receiver however, comprises a controller 201 configured to receive the output of the detector and/or to feed the emitter. This may be performed via electrical connections 202 through the receiver housing wall. Naturally, electrical conductors to/from the emitter/detector/controller are also desired. In this manner, the controller is protected in the receiver and may be connected to the emitter/detector later. Clearly, the emitter/detector may alternatively be provided in the receiver housing if desired.

The connections 202 may also be used for receiving information or power to the controller 201 from an external source, such as a battery or another controller. Also, the connections may be used for outputting a signal from the controller 201. The controller 201 may analyse the information output of the detector(s) and then output a result of this analysis, such as a pulse of the person. Alternatively, the controller 201 may output the data received from the detector(s) or a result of an analysis thereof, which result requires further analysis of the external controller.

If further detectors or sensors are provided, these may also be provided in the receiver housing or outside thereof and connected to the controller in the same manner. Such sensors may be used for e.g. determining an orientation of the person or assembly.

Also, the receiver(s) may be controlled so as to only be operated at particular points in time, such as according to a schedule. If multiple receivers are provided, one or more may be operated and others not. The controller may facilitate this control.

Also, the controller may perform noise cancelling or reduction of the signals from the detectors if desired.

Thus, the present assembly may be used, as described, in a hearing aid or hearable. Naturally, such hearing aid or hearable may comprise other elements, such as a battery, antenna or coil, processor, amplifier, other circuits, or the like.

EMBODIMENTS

1. An assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing.

2. A method of providing an assembly according to embodiment 1, the method comprising connecting the emitter(s) and detector(s) to the housing.

3. The assembly according to embodiment 1, wherein one or more of the detector(s) and/or one or more of the emitter(s) is/are configured to be directed at least substantially in a vertical direction.

4. The method of embodiment 2, comprising the step of positioning the assembly in the ear canal of a person so that one or more of the detector(s) and/or one or more of the emitter(s) is/are directed at least substantially in a vertical direction.

5. The assembly according to embodiment 1 or 3, wherein:
  one of the radiation detectors is positioned in or at the housing and has a field of view defining a view axis,
  one of the radiation emitters is positioned in or at the housing and has an emission cone defining an emission axis.

6. The assembly of embodiment 5, wherein no overlap exists between the field of view and the emission cone within a distance of 0 mm from the housing.

7. The assembly of embodiment 6, wherein there is no overlap between the field of view and the emission cone.

8. The assembly of any of embodiment 5-7, wherein the housing comprises at least a first and a second non-overlapping surface parts directed in different directions, where:
  the view axis of one of the detector(s) extends at an angle, such as an angle in the interval of 30-160 degrees, such as within the interval of 45-135 degrees, such as around 90 degrees, to the first surface part and
  the emission axis of one of the emitter(s) extends at an angle, such as an angle in the interval of 30-160 degrees, such as within the interval of 30-160 degrees, such as within the interval of 45-135, such as around 90 degrees to the second surface part.

9. The assembly according to embodiment 8, wherein the housing has 6 surface portions, pairwise at least substantially parallel, where each pair of surface portions are at least substantially perpendicular to the other pairs of surface portions, the first surface portion being one of the 6 surface portions.

10. The assembly according to embodiment 9, wherein the second surface portion extends between at least two of the 6 surface portions and has a non-zero angle to each of the at least two of the 6 surface portions.

11. The method according to embodiment 2 or 4, wherein:
  one of the radiation detectors detects radiation within a field of view defining a view axis,
  one of the radiation emitters emits radiation within an emission cone defining an emission axis.

12. The method of embodiment 11, wherein there is no overlap between the field of view and the emission cone.

13. The method of embodiment 12, wherein no overlap exists between the field of view and the emission cone within a distance of 1 mm from the housing.

14. The method of any of embodiment 11-13, wherein the housing comprises at least a first and a second non-overlapping surface parts directed in different directions, where:
  the view axis of one of the detector(s) extends at an angle, such as an angle in the interval of 30-160 degrees, such as within the interval of 45-135 degrees, such as around 90 degrees, to the first surface part and
  the emission axis of one of the emitter(s) extends at an angle, such as an angle in the interval of 30-160 degrees, such as within the interval of 30-160 degrees, such as within the interval of 45-135, such as around 90 degrees to the second surface part.

15. The method according to embodiment 14, wherein the housing has 6 surface portions, pairwise at least substantially parallel, where each pair of surface portions are at least substantially perpendicular to the other pairs of surface portions, the first surface portion being one of the 6 surface portions.

16. The method according to embodiment 15, wherein the second surface portion extends between at least two of the 6 surface portions and has a non-zero angle to each of the at least two of the 6 surface portions.

17. An assembly of a receiver, a radiation emitter, a radiation detector and an assembly housing, wherein:
the receiver has a receiver housing and is positioned inside the assembly housing,
the radiation detector is positioned in the assembly housing and has a reception direction along a first direction,
the radiation emitter is positioned in the assembly housing and has an emission direction along a second direction, an angle existing between the first and second directions,
one or more windows transparent to the radiation are provided in the assembly housing for allowing radiation from the emitter to exit the assembly housing and radiation from outside of the assembly housing to reach the detector.

18. An assembly according to embodiment 17, wherein the assembly housing is arranged to have the radiation emitter or radiation emitter positioned in ear canal to allow radiation to exit towards or enter from the direction towards the bottom of the ear canal.

19. The assembly according to any of embodiments 1, 3, 5-10 and 17-18 wherein:
one of the radiation detectors is positioned in the housing and has a field of view, and
one of the radiation emitters is positioned in the housing and has an emission cone,
where a distance of at least 1 mm exists between the field of view and the cone, within a distance of at least 0 mm from the housing.

20. The assembly of embodiment 19, wherein the housing is configured to engage an ear canal at a position comprised within the field of view or the cone.

21. The assembly of embodiment 19 or 20, wherein the field of view and/or cone is defined by a window and/or a lens at the outer surface of the housing.

22. A method according to any of embodiments 2, 4, and 11-16 wherein:
one of the radiation detectors receives radiation within a field of view,
one of the radiation emitters emits radiation within an emission cone, where a distance of at least 1 mm exists between the field of view and the cone, within a distance of at least 1 mm from the housing.

23. The method of embodiment 22, wherein the housing engages an ear canal at a position comprised within the field of view or the cone.

24. The method of embodiment 22 or 23, wherein the field of view and/or cone is defined by a window and/or a lens at the outer surface of the housing.

25. The assembly according to any of embodiments 1, 3, 5-10, and 17-21, further comprising a receiver having a receiver housing, wherein at least one of the one or more detectors and one or more emitters is attached to the receiver housing.

26. The assembly of embodiment 25, further comprising a first window or lens in the receiver housing and a second window or lens in either the housing or an element attached to the housing, wherein an emitter is positioned so as to emit radiation toward one of the first and second window/lens and a detector is positioned so as to receive radiation via another of the first and second window/lens.

27. An assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing,
the sensor comprises a radiation emitter and a radiation detector,
the receiver housing at least one of the emitter and the detector overlap at least partly when projected on to a first plane, and
the receiver housing and the at least one of the emitter and the detector overlap at least partly when projected on to a second plane perpendicular to the first plane.

28. An assembly according to embodiment 27, further comprising an additional element attached to the receiver, one of the emitter and the detector being attached to the additional element.

29. An assembly according to embodiment 27 or 28, wherein:
the detector has a field of view having a first central axis,
the emitter defines an emission cone having a second central axis, where a non-zero angle exists between the first and second central axes.

30. An assembly according to any of embodiments 27-29, wherein the receiver housing has a number of at least substantially plane surface parts, wherein the detector is provided in or at a first of the surface parts and the emitter is provided in or at a second of the surface parts.

31. The method according to any of embodiments 2, 4, 11-16, and 22-24 further comprising a receiver having a receiver housing, wherein at least one of the one or more detectors and one or more emitters is attached to the receiver housing.

32. The method of embodiment 31, wherein an emitter is positioned so as to emit radiation toward one of a first and a second window/lens and a detector is positioned so as to receive radiation via another of the first and second window/lens, the first window or lens being provided in or at the receiver housing and the second window or lens being positioned in or at either the housing or an element attached to the housing, 33. A method of providing an assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing, and
the sensor comprises a radiation emitter and a radiation detector,
the method comprising providing the receiver and the sensor so that:
the receiver housing at least one of the emitter and the detector overlap at least partly when projected on to a first plane, and
the receiver housing and the at least one of the emitter and the detector overlap at least partly when projected on to a second plane perpendicular to the first plane.

34. A method according to embodiment 33, further comprising an additional element attached to the receiver, one of the emitter and the detector being attached to the additional element.

35. A method according to embodiment 33 or 34, wherein:
the detector receives radiation in a field of view having a first central axis,
the emitter outputs radiation in an emission cone having a second central axis, where a non-zero angle exists between the first and second central axes.

36. An assembly according to any of embodiments 33-35, wherein the receiver housing has a number of at least substantially plane surface parts, wherein the detector is provided in or at a first of the surface parts and the emitter is provided in or at a second of the surface parts.

37. The assembly according to any of the preceding embodiments 1, 3, 5-10, 17-21, and 25-30, wherein:
one of the radiation detectors is positioned in the housing and has a field of view,
one of the radiation emitters is positioned in the housing and has an emission cone,
the assembly further comprising a radiation blocking element provided in an overlap between the field of view and the cone.

38. The assembly according to embodiment 37, wherein the radiation blocking element engages the housing or is fixed to the housing and extends away from the housing.

39. The method according to any of the preceding embodiments 2, 4, 11-16, 22-24, and 31-35 wherein:
one of the radiation detectors is positioned in the housing and receives radiation within a field of view,
one of the radiation emitters is positioned in the housing and emits radiation within an emission cone,
the method further comprising blocking radiation travelling in an overlap between the field of view and the cone.

40. The method according to embodiment 39, wherein the blocking step comprises blocking the radiation with a radiation blocking element engages the housing or is fixed to the housing and extends away from the housing.

41. The assembly according to any of embodiments 1, 3, 5-10, 17-21, 25-30, and 36-38, further comprising a receiver, wherein:
the receiver comprises:
a receiver housing with a receiver housing wall part comprising a sound output,
a receiver diaphragm defining, with an inner surface of the receiver housing, a first chamber in the receiver housing,
one of the one or more detectors and one or more emitters comprises a sensor housing,
the receiver housing and the sensor housing overlap at least partly when projected on to a first plane, and
the receiver housing and sensor housing overlap at least partly when projected on to a second plane perpendicular to the first plane.

42. The assembly according to any of embodiments 1, 3, 5-10, 17-21, 25-30, and 36-38, further comprising a receiver, wherein:
the receiver comprises:
a receiver housing,
a receiver diaphragm defining, with an inner surface of the receiver housing, a first chamber in the receiver housing having a sound output, and a second chamber in the receiver housing,
one of the one or more detectors and one or more emitters comprises a sensor housing being at least partially inside the second chamber, and
the sensor housing or its portion inside the second chamber, having a volume not exceeding 20% of a volume of the second chamber.

43. An assembly comprising a receiver and a sensor, wherein:
the receiver comprises:
a receiver housing,
a receiver diaphragm defining, with an inner surface of the receiver housing, a first chamber in the receiver housing having a sound output, and a second chamber in the receiver housing,
the sensor comprises a sensor housing being at least partially inside the second chamber, and
the sensor housing or its portion inside the second chamber, having a volume not exceeding 20% of a volume of the second chamber.

44. An assembly comprising a sensor and a receiver, wherein:
the receiver comprises:
a receiver housing with a receiver housing wall part comprising a sound output,
a receiver diaphragm defining, with an inner surface of the receiver housing, a first chamber in the receiver housing,
the sensor comprises a sensor housing,
the receiver housing and sensor housing overlap at least partly when projected on to a first plane, and
the receiver housing and sensor housing overlap at least partly when projected on to a second plane perpendicular to the first plane.

45. An assembly according to embodiment 44, wherein the sensor housing is positioned at least partly inside the receiver housing.

46. An assembly according to embodiment 45, wherein the sensor housing has an outer volume not exceeding 20% of an inner volume of the receiver housing.

47. An assembly according to any of embodiments 43-46, wherein the sensor housing is positioned at least partly outside of the receiver housing.

48. An assembly according to embodiment 47, wherein the sensor housing is attached to the receiver housing.

49. An assembly according to embodiment 47 or 48, further comprising one or more conductors connected to the sensor housing and extending outside of the sensor housing, at least a part of the conductor(s) extending inside the receiver housing.

50. An assembly according to any of embodiments 43-49, wherein the receiver diaphragm and sensor housing overlap at least partly when projected on to a first plane.

51. An assembly according to any of embodiments 43-50, wherein the receiver housing and sensor housing, when projected on to a first plane, overlap an area of at least 10% of an area of the sensor housing in the projection.

52. An assembly comprising a receiver and a sensor, wherein:
the receiver comprises:
a receiver housing,
a receiver diaphragm defining, with an inner surface of the receiver housing, a first chamber in the receiver housing having a sound output, and a second chamber in the receiver housing,
the sensor comprises a radiation emitter and a radiation detector, one of the radiation emitter and the radiation detector being at least partially inside the second chamber.

53. An assembly according to embodiment 52, wherein the portion of the one of the emitter and the detector inside the second chamber has a volume not exceeding 20% of a volume of the second chamber.

54. The method according to any of embodiments 2, 4, 11-16, 22-24, 31-35, 39, and 40 further comprising operating a receiver, comprising:
   a receiver housing with a receiver housing wall part comprising a sound output,
   a receiver diaphragm defining, with an inner surface of the receiver housing, a first chamber in the receiver housing,
   the method comprising providing the housing, a sensor with a sensor housing and the receiver so that:
   the receiver housing and a sensor housing overlap at least partly when projected on to a first plane, and
   the receiver housing and sensor housing overlap at least partly when projected on to a second plane perpendicular to the first plane.

55. The method according to any of embodiments 2, 4, 11-16, 22-24, 31-35, 39, and 40 further comprising operating a receiver comprising:
   a receiver housing,
   a receiver diaphragm defining, with an inner surface of the receiver housing, a first chamber in the receiver housing having a sound output, and a second chamber in the receiver housing,
   the method comprising providing the housing, a sensor with a sensor housing and the receiver so that:
   one of the one or more detectors and one or more emitters comprises a sensor housing being at least partially inside the second chamber, and
   the sensor housing or its portion inside the second chamber, having a volume not exceeding 20% of a volume of the second chamber.

56. A method of providing an assembly of a receiver and a sensor, wherein:
   the receiver comprises:
      a receiver housing,
      a receiver diaphragm defining, with an inner surface of the receiver housing, a first chamber in the receiver housing having a sound output, and a second chamber in the receiver housing, and
   the sensor comprises a sensor housing being at least partially inside the second chamber,
   the method comprising providing the sensor housing or its portion inside the second chamber, having a volume not exceeding 20% of a volume of the second chamber.

57. A method of providing an assembly comprising a sensor and a receiver, wherein:
   the receiver comprises:
      a receiver housing with a receiver housing wall part comprising a sound output,
      a receiver diaphragm defining, with an inner surface of the receiver housing, a first chamber in the receiver housing,
   the sensor comprises a sensor housing,
   the method comprising providing the receiver and sensor so that:
   the receiver housing and sensor housing overlap at least partly when projected on to a first plane, and
   the receiver housing and sensor housing overlap at least partly when projected on to a second plane perpendicular to the first plane.

58. A method according to embodiment 75, wherein the sensor housing is positioned at least partly inside the receiver housing.

59. A method according to embodiment 58, wherein the sensor housing has an outer volume not exceeding 20% of an inner volume of the receiver housing.

60. A method according to any of embodiments 55-59, wherein the sensor housing is box-shaped and has 6 outer wall portions, where a wall portion with a largest surface area has a surface area not exceeding twice a surface area of a wall portion having the smallest surface area.

61. A method according to any of embodiments 54-60, wherein the sensor housing is positioned at least partly outside of the receiver housing.

62. A method according to embodiment 61, wherein the sensor housing is attached to the receiver housing.

63. A method according to embodiment 61 or 62, further comprising one or more conductors connected to the sensor housing and extending outside of the sensor housing, at least a part of the conductor(s) extending inside the receiver housing.

64. A method according to any of embodiments 54-63, wherein the receiver diaphragm and sensor housing overlap at least partly when projected on to a first plane.

65. A method according to any of embodiments 54-64, wherein the receiver housing and sensor housing, when projected on to a first plane, overlap an area of at least 10% of an area of the sensor housing in the projection.

66. A method comprising providing an assembly of a receiver and a sensor, wherein:
   the receiver comprises:
      a receiver housing,
      a receiver diaphragm defining, with an inner surface of the receiver housing, a first chamber in the receiver housing having a sound output, and a second chamber in the receiver housing,
   the sensor comprises a radiation emitter and a radiation detector, one of the radiation emitter and the radiation detector being at least partially inside the second chamber.

67. A method according to embodiment 66, wherein the portion of the one of the emitter and the detector inside the second chamber has a volume not exceeding 20% of a volume of the second chamber.

68. The assembly according to any of embodiments 1, 3, 5-10, 17-21, 25-30, 36-38, and 41-53 wherein:
   the radiation detector(s) are positioned in or symmetrically on either side of a plane extending through the housing and/or
   the radiation emitter(s) is/are positioned in or symmetrically on either side of the plane.

69. The assembly according to embodiment 68, wherein the housing is configured to be positioned so that the plane is at least substantially vertical.

70. The assembly according to embodiment 68 or 69, wherein at least one detector is positioned to receive radiation travelling in the plane.

71. The method according to any of embodiments 2, 4, 11-16, 22-24, 31-35, 39, 40, and 54-67 comprising:
   positioning the radiation detector(s) in or symmetrically on either side of a plane extending through the housing and/or
   positioning the radiation emitter(s) in or symmetrically on either side of the plane.

72. The method according to embodiment 71, wherein the housing is positioned in an ear canal so that the plane is at least substantially vertical.

73. The method according to embodiment 71 or 72, wherein at least one detector is positioned to receive radiation travelling in the plane.

74. The method according to any of embodiments 71-73, comprising providing two of the assemblies and providing one in a left ear canal of a person and the other in the right ear canal of the person.

75. The assembly according to any of embodiments 1, 3, 5-10, 17-21, 25-30, 36-38, 41-53, 68-70, wherein the housing is oblong with a first end portion and a second, opposite end portion, the housing comprising a sound outlet in or at the first end portion, where a majority of the radiation emitter(s) and a majority of the radiation detector(s) is/are positioned closer to the first end portion than the second end portion.

76. The assembly according to embodiment 75, the assembly further comprising a receiver positioned in the housing, where a majority of the radiation emitters and the radiation detectors are positioned, in a projection on to a longitudinal axis of the housing, closer to the first end portion than a centre of the receiver.

77. The method according to any of embodiments 2, 4, 11-16, 22-24, 31-35, 39, 40, 54-67, and 71-74, wherein the housing is oblong with a first end portion and a second, opposite end portion, the housing comprising a sound outlet in or at the first end portion, the method comprising positioning a majority of the radiation emitter(s) and a majority of the radiation detector(s) closer to the first end portion than the second end portion.

78. The method according to embodiment 77, further comprising positioning a receiver in the housing, where the step of positioning the majority of the radiation detector(s) and the majority of the radiation emitter(s) comprises positioning a majority of the radiation emitters and the radiation detectors are positioned, in a projection on to a longitudinal axis of the housing, closer to the first end portion than a centre of the receiver.

The invention claimed is:

1. An assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing, the assembly further comprising a receiver, wherein:
the receiver comprises:
a receiver housing,
a receiver diaphragm defining, with an inner surface of the receiver housing, a first chamber in the receiver housing having a sound output, and a second chamber in the receiver housing,
one of the one or more detectors and one or more emitters comprises a sensor housing being at least partially inside the second chamber, and
the sensor housing or its portion inside the second chamber, having a volume not exceeding 20% of a volume of the second chamber.

2. The assembly according to claim 1, wherein one or more of the detector(s) and/or one or more of the emitter(s) is/are configured to be directed at least substantially in a vertical direction.

3. The assembly according to claim 1, wherein:
one of the radiation detectors is positioned in or at the housing and has a field of view defining a view axis,
one of the radiation emitters is positioned in or at the housing and has an emission cone defining an emission axis,
wherein there is no overlap between the field of view and the emission cone.

4. The assembly according to claim 1, wherein:
one of the radiation detectors is positioned in the housing and has a field of view, and
one of the radiation emitters is positioned in the housing and has an emission cone, where a distance of at least 0 mm exists between the field of view and the cone, within a distance of at least 1 mm from the housing.

5. The assembly according to claim 4, wherein at least one of the one or more detectors and one or more emitters is attached to the receiver housing.

6. The assembly according to claim 1, wherein:
one of the radiation detectors is positioned in the housing and has a field of view,
one of the radiation emitters is positioned in the housing and has an emission cone,
the assembly further comprising a radiation blocking element provided in an overlap between the field of view and the cone.

7. The assembly according to claim 1, wherein the receiver housing includes a receiver housing wall part including a sound output,
the receiver housing and the sensor housing overlap at least partly when projected on to a first plane, and
the receiver housing and sensor housing overlap at least partly when projected on to a second plane perpendicular to the first plane.

8. The assembly according to claim 1, wherein:
the radiation detector(s) are positioned in or symmetrically on either side of a plane extending through the housing and/or
the radiation emitter(s) is/are positioned in or symmetrically on either side of the plane.

9. The assembly according to claim 1, wherein the housing is oblong with a first end portion and a second, opposite end portion, the housing comprising a sound outlet in or at the first end portion, where a majority of the radiation emitter(s) and a majority of the radiation detector(s) is/are positioned closer to the first end portion than the second end portion.

10. A method of operating an assembly of claim 1 being adapted for a universal fitting in either a left or a right ear canal of a person, the method comprising the steps of:
providing the assembly in one of the left and the right ear canal,
feeding information to the assembly as to which of the left and right ear canal the assembly was provided in,
operating the assembly in accordance with the information.

11. A method of operating an assembly of claim 1, the method comprising the steps of:
determining relative movement between an ear canal and the assembly housing and operating in accordance with the relative movement determined;
generating a control signal to adjust the operation of the assembly.

12. An assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing, wherein:
one of the radiation detectors is positioned in the housing and has a field of view, and
one of the radiation emitters is positioned in the housing and has an emission cone, where a distance of at least 0 mm exists between the field of view and the cone, within a distance of at least 1 mm from the housing.

13. An assembly of at least one radiation detector, at least one radiation emitter and a housing configured to be positioned inside the ear canal of a person or animal, the detector(s) and emitter(s) being provided in or on the housing, the emitter(s) being configured to emit radiation away from the housing and the detector(s) being configured to receive radiation directed toward the housing, further comprising a receiver, wherein:

the receiver comprises:
- a receiver housing with a receiver housing wall part comprising a sound output,
- a receiver diaphragm defining, with an inner surface of the receiver housing, a first chamber in the receiver housing, one of the one or more detectors and one or more emitters comprises a sensor housing, the receiver housing and the sensor housing overlap at least partly when projected on to a first plane, and the receiver housing and sensor housing overlap at least partly when projected on to a second plane perpendicular to the first plane.

* * * * *